United States Patent
O'Brien

(12) 
(10) Patent No.: US 10,637,900 B2
(45) Date of Patent: Apr. 28, 2020

(54) COMPUTERIZED NETWORK SYSTEM FOR INITIATING, FACILITATING, AUDITING, AND MANAGING COMMUNICATIONS AND DOCUMENTS INVOLVING PROFESSIONAL EXPERTISE

(71) Applicant: Beatrice T. O'Brien, Short Hills, NJ (US)

(72) Inventor: Beatrice T. O'Brien, Short Hills, NJ (US)

(*) Notice: Subject to any disclaimer, the term of this patent is extended or adjusted under 35 U.S.C. 154(b) by 168 days.

(21) Appl. No.: 16/041,070

(22) Filed: Jul. 20, 2018

(65) Prior Publication Data

US 2019/0182299 A1 Jun. 13, 2019

Related U.S. Application Data

(60) Provisional application No. 62/596,192, filed on Dec. 8, 2017, provisional application No. 62/629,354, filed
(Continued)

(51) Int. Cl.
*H04L 29/06* (2006.01)
*G16H 80/00* (2018.01)
*G06Q 50/18* (2012.01)

(52) U.S. Cl.
CPC .......... *H04L 65/403* (2013.01); *G06Q 50/18* (2013.01); *G16H 80/00* (2018.01); *H04L 63/12* (2013.01);
(Continued)

(58) Field of Classification Search
CPC ..................................................... H04L 65/403
See application file for complete search history.

(56) References Cited

U.S. PATENT DOCUMENTS 6,678,698 B2 * 1/2004 Fredell ................. G06Q 10/06
                                                            707/608
7,167,855 B1 * 1/2007 Koenig ................. G06Q 30/02
(Continued)

FOREIGN PATENT DOCUMENTS

WO      WO0133936 A1    5/2001
WO      WO0175628 A1   10/2001
(Continued)

OTHER PUBLICATIONS

Dubovitskaya, Alevtina et al. "Secure and Trustable Electronic Medical Records Sharing using Blockchain." AMIA Annual Symposium proceedings. AMIA Symposium vol. 2017 650-659. Apr. 16, 2018. (Year: 2018).*
(Continued)

*Primary Examiner* — Jacob C. Coppola
(74) *Attorney, Agent, or Firm* — Thomas J. Germinario

(57) ABSTRACT

A computerized network links individual lay users, referred to as "standard users," with qualified professionals in one or more disciplines, such as law, medicine, engineering, accounting and architecture, who are referred to as "participating professionals." Business entities, such as corporations, partnerships and limited liability companies, can also participate as "enterprise users," with linkage through the network to both standard users and participating professionals. The network enables standard users, participating professionals and enterprise users to communicate, share information, conduct studies, and negotiate and/or create documents relating to the professional disciplines.

20 Claims, 24 Drawing Sheets

Related U.S. Application Data on Feb. 12, 2018, provisional application No. 62/632,718, filed on Feb. 20, 2018, provisional application No. 62/668,496, filed on May 8, 2018.

(52) U.S. Cl.
CPC ...... *H04L 65/4007* (2013.01); *H04L 65/4015* (2013.01); *H04L 63/04* (2013.01)

(56) References Cited

U.S. PATENT DOCUMENTS

| | | |
|---|---|---|
| 8,086,699 B2 | 12/2011 | Christopher |
| 9,613,190 B2 * | 4/2017 | Ford ........................ G06F 21/10 |
| 9,703,760 B2 | 7/2017 | O'Donoghue et al. |
| 2002/0022972 A1 | 2/2002 | Costello |
| 2002/0124188 A1 * | 9/2002 | Sherman ................ G06Q 10/10 |
| | | 726/6 |
| 2002/0194033 A1 | 12/2002 | Huff |
| 2004/0103040 A1 * | 5/2004 | Ronaghi ............ G06K 13/0825 |
| | | 705/14.69 |
| 2006/0004623 A1 | 1/2006 | Jasti |
| 2008/0065726 A1 * | 3/2008 | Schoenberg ..... G06Q 10/06375 |
| | | 709/205 |
| 2009/0089098 A1 * | 4/2009 | Schoenberg ........... G06Q 50/22 |
| | | 705/3 |
| 2010/0332974 A1 | 12/2010 | Thomas |
| 2011/0137823 A1 * | 6/2011 | Robb ........................ G06F 9/54 |
| | | 705/36 R |
| 2013/0179494 A1 * | 7/2013 | Chakravarthy ........ H04N 21/80 |
| | | 709/203 |
| 2015/0261917 A1 * | 9/2015 | Smith ................ G06F 21/6263 |
| | | 705/3 |
| 2016/0012739 A1 * | 1/2016 | Jafari ........................ G09B 5/06 |
| | | 434/353 |
| 2016/0156699 A1 | 6/2016 | Boemer |
| 2017/0041296 A1 * | 2/2017 | Ford ........................ H04W 12/02 |
| 2017/0046638 A1 * | 2/2017 | Chan ................. G06Q 20/3829 |

FOREIGN PATENT DOCUMENTS

| | | |
|---|---|---|
| WO | WO0225404 A2 | 3/2002 |
| WO | WO2016094407 A1 | 6/2016 |

OTHER PUBLICATIONS

PCT International Search Report for PCT/US18/57099, dated Dec. 27, 2018.

* cited by examiner

Legal Main Screen

Fluid UI □ 12:30

Create Participant Profile

Welcome JohnDoe@gmail.com! You have been invited to participate in the Northgate Digital Drug Trial. Please complete the below fields to complete your LawPlain registration.

First Name
Last Name
Question (Y/N) >
Question (On/Off) ⬤

Save and Continue

FIG. 16B

Fluid UI □ 12:30

Create Lawyer Profile

Welcome JohnDoe@gmail.com! You have been invited to participate in the Northgate Digital Drug Trial. Please complete the below fields to complete your LawPlain registration.

First Name
Last Name
Areas of Expertise
Years Practicing Law    7

Save and Continue 9
8
7
6
5

FIG. 16C

Fluid UI □ 12:30

< Back    Area of Expertise

Item >
Item >
Item >
Item >
Item

Authentication

FIG. 17A

Screens 1.0–3.0

1.0 Q&A
- 1.1 Search Topics
- 1.2 Ask a Question
- 1.3 View & Reply

2.0 Messaging
- 2.1 Conversations
- 2.2 Chat
- 2.3 Attachments

3.0 Documents
- 3.1 List Documents
- 3.2 View Document
- 3.3 Sign Document
- 3.4 Term Lookup
- 3.5 Record Consent

FIG. 17B

Screens 4.0–6.0

4.0 Settings
- 4.1 Profile
- 4.2 Billing

5.0 Studies
- 5.1 List Studies
- 5.2 Manage Participants
- 5.3 Invite Participant
- 5.4 Manage Staff

6.0 Authentication
- 6.1 Login
- 6.2 Register
- 6.3 Password Reset

FIG. 18C 2.0–Messaging/Chart

FIG. 20E 4.0–Settings/Profile

Fluid UI    12:30

Profile/Settings

[ Profile | Billing ]

First name
[ Kate ]

Last name
[ Smith ]

Address
[ 301 South State Street ]

City
[ Newtown ]

State
[ Pennsylvania ]

Zip
[ 18940 ]

Change Password
[ New Password ] [ Confirm Password ]

Important Links
LawPlain Blog   Privacy Policy   Terms

Questions   Chat   Documents   Study   Settings

FIG. 21A

Fluid UI    12:30

Profile/Settings

[ Profile | Billing ]

Subscription
Subscription type:   Legal
Active until:   May 20, 2019
Cost:   $200 per month

[ Update Subscription ]

Questions   Chat   Documents   Study   Settings

| Fluid UI | 🗂 12:30 |
|---|---|
| Study A | |

| Staff A | 💬 |
| Staff B | 💬 |
| Staff C | 💬 |
| Staff D | 💬 |

( + )

Questions | Chat | Documents | Study | ⚙ Settings

FIG. 22B

5.0—Study Management

| Fluid UI | 🗂 12:30 |
|---|---|
| Participant List | |

| Name | Status | Contact |
|---|---|---|
| Participant A | ⊙ | 💬 |
| Participant B | | 💬 |
| Participant C | ⊙ | 💬 |
| Participant D | | 💬 |

( + )

Questions | Chat | Documents | Study | ⚙ Settings

FIG. 22C

| Fluid UI | 🗂 12:30 |
|---|---|
| Study A | |

[▷ video thumbnail]   ^
^
Study Name   ^
Study Description
Upload Study Documents Questions | Chat | Documents | Study | ⚙ Settings

5.0–Study Management

Fluid UI 🗓 12:30

Send Document

< Back

Recipient: John Doe
File: study-xyz.pdf
Require recorded consent

[ Send ]

Attach media
🎙 Recording | 💬 Chat | 🖼 Image/Video | 📄 Documents | 📄 Document | ⚙ Settings
📋 Questions

Fluid UI 🗓 12:30

Participant List

| Name | Status | Contact |
|---|---|---|
| Participant A | ⊘ | 💬 |

Invite Participant
Enter an email address to invite a participant to this study someone@gmail.com

[ Cancel ] [ Invite ]

(+)

📋 Questions | 💬 Chat | 📄 Documents | ⊞ Study | ⚙ Settings

FIG. 22E

COMPUTERIZED NETWORK SYSTEM FOR INITIATING, FACILITATING, AUDITING, AND MANAGING COMMUNICATIONS AND DOCUMENTS INVOLVING PROFESSIONAL EXPERTISE

REFERENCE TO RELATED APPLICATIONS

This application claims the benefit of the filing dates of U.S. Provisional Applications Nos. 62/596,192 (filed Dec. 8, 2017), 62/629,354 (Feb. 12, 2018), 62/632,718 (Feb. 20, 2018), and 62/668,496 (filed May 8, 2018), the disclosures of which are incorporated herein by reference.

FIELD OF INVENTION

The present invention relates generally to the fields of networked digital communications and documents and computerized systems for initiating, facilitating, auditing, and managing such communications and documents, and more particularly to applications of such systems to communications and documents involving one or more fields of professional expertise.

BACKGROUND OF THE INVENTION

When a lay person is seeking advice or explanations concerning a professional discipline, such as law or medicine, or regarding documents relating to that discipline, the time and expense involved in making an appointment with a qualified professional can be an inhibiting factor. Conversely, professionals are often reluctant to give informal advice because of potential liability issues involving the content of the communications, possible conflicts-of-interest and confidentiality.

While various websites offer information and/or respond to questions pertaining to professional expertise, the ability of the inquirer to interact in real time with a qualified professional is absent or very limited. Ethical constraints can also make it difficult for professionals to initiate direct communications with members of the public with whom they have had no previous relationship.

This state of affairs works to the disadvantage of both inquiring lay people and potentially helpful professionals. The former are deprived of information vital to their personal and financial affairs, and the latter lose the opportunity to interact with potential clients or patients.

The present invention responds to this dilemma by providing an integrated computerized system using downloadable and web-based application software ("Apps") to initiate, manage and track exchanges of information and documents between lay users, including both individual and business enterprises, and qualified professionals, as well as between and among individual and enterprise users themselves. The features of the Apps, as described further herein, assure that all such interactions proceed in accordance with all applicable legal and ethical requirements for obtaining users' informed consent and protecting users' confidential information. Compliance with such requirements is documented by an audit trail compiled by the Apps and stored in a system database for the protection of both participating users and professionals, so that impediments to the flow of information and guidance on professional topics are minimized.

SUMMARY OF THE INVENTION

The system of the present invention comprises a computerized network which links individual lay users, hereinafter referred to as "standard users," with qualified professionals in one or more disciplines, such as law, medicine, engineering, accounting and architecture, who are hereinafter referred to as "participating professionals." Business entities, such as corporations, partnerships and limited liability companies, can also participate as "enterprise users," with linkage through the network to both standard users and participating professionals.

For standard users, the system provides a downloadable native User App, which runs on a smartphone, tablet or other personal computing device (hereinafter collectively referred to as a "pc device"). Enterprise users participate through a Web App, which runs on a web platform maintained by the System Server. Participating professionals are provided with a downloadable native Professional App, which runs on a pc device and links to the Web App.

The hardware architecture of the system network 110 is depicted schematically in FIG. 1, which shows the standard user pc devices 111, enterprise pc devices 112, professional pc devices 113, the connecting internet 114, the System Server 115, and the System Database 115A. As will be explained subsequently herein, the system network 110 also enables private communications path 116 between a standard user 111 and a professional 113 with whom the standard user 111 has established a client or patient relationship, so as to protect the confidentiality of client/patient information.

The User App provides a top menu comprising a User Login page, a Home Screen and a User's Tool Menu. The User's Tool Menu comprises option tabs for Connect, Profile, Files, Upload, Chat, and Professional Services. The Connect option enables standard users to engage with other standard users and enterprise users in discussion forums, categorized by topics and hashtags relating to the relevant professional discipline. Through the Profile tab, users manage their personal settings, as well as app notifications and alerts.

Under the Files tab, the user can view the status of documents, highlight terms within a document for definition, open a live chat with a professional from within the document, or agree to the document by voice (VoIP) recording or touch screen confirmation. In the Chat option, users can open a live chat consultation with a qualified professional by selecting a professional discipline and a specialty area within that discipline. The "in-App calling" feature allows the user and/or the professional to select a live chat mode of text, VOIP call or video chat. Documents and files relevant to the professional consultation can be uploaded via the Upload option, and the user can highlight sections of a document or file to which their inquiry pertains.

When the standard user shares files and/or documents with participating professionals, the User App advises them of their privacy rights and obtains their informed consent to the information disclosures. All shared user information and user-professional communications are recorded and preserved in an audit trail, the immutability of which can be protected using blockchain technology.

The User and Professional Apps restrict access to shared user information and user-professional communications to the respective user and professional and maintain an immutable audit trail of the confidential handling of such information and communications. In the event a user enters into a formal client or patient relationship with a participating professional, the Apps route subsequent communications and information disclosures on a private basis between the user and the professional.

The Professional App provides a top menu comprising a Professional Login Page, a Home Screen and a Professional's Tool Menu. The Professional's Tool Menu comprises option tabs for Web App link, Profile, Files, Chat, and Proposals. The initial Professional Login includes a setup of the Professional App, which elicits the professional's qualifications, specialty areas, experience, and permissions/licenses, as well as billing information and terms associated with their participation in one or more of the service plans provided by the system.

Under the Files option, the professional accesses a list of documents and files relating to standard users with whom he/she has interacted, sees the status of each document/file, displays the entire document/file, and receives prompts for actions required in connection therewith. From the Chat tab, the professional accesses an itemized list of chats they have open with standard users and enterprise users (through the Web App). A specific chat item can be selected to open a chat window with the respective user. The Professional App incorporates informed consent, confidentiality and audit trail features corresponding to those described above with reference to the User App.

Enterprise users access the system network through the Web App, which is also accessible to professionals. The Web App has a top menu comprising a Login Page and a Dashboard Main Menu. Initial setup of an enterprise account involves selection of a service plan and associated billing information. The Dashboard enables the enterprise user to upload documents, including legal agreements, which are intended for one or more standard users. The system offers plan services that include staff review of enterprise documents and identification of problems needing corrective action. Depending on the selected service plan, document review can include consultation with a staff lawyer regarding legal issues pertaining to the document.

The Web App also includes a Group Chat option, through which enterprise users can engage in group chats with multiple invited standard users, professionals and/or other enterprise users. The Group Chat option allows the participants to choose between chat modes of text, VOIP or video chat. Invited parties must sign a Non-Disclosure Agreement (NDA) uploaded by the initiating enterprise user prior to joining the group chat. Within the group chat, documents can be shared by the initiating enterprise user.

The present invention also provides a platform for the initiation of professional services agreements between participating professionals and standard and/or enterprise users. The User App and the Web App each have a Professional Services Menu, by which a standard or enterprise user can request that participating professionals submit proposals for specified professional services, through a Proposals Menu in the Professional App. Conversely, the Proposals Menu of the Professional App also enables the participating professionals to offer specified professional services at specified fixed fees to standard and/or enterprise users, who can accept the offers through the Professional Services Menu of the User or Web App.

The User App and the Web App also incorporate, under the Professional Services Menu, a Proposal Qualification/Evaluation option. In the Proposal Qualification/Evaluation option, a standard user or an enterprise user can specify minimum qualifications for participating professionals submitting proposals and/or multiple proposal evaluation criteria, by which the App can generate a "short list" of qualifying proposals and/or a ranking of proposals based on the evaluation criteria.

In many instances, the documents associated with professional services comprise forms, which are generated and periodically updated by governmental or private entities. The present invention incorporates software which automatically updates all such professional forms, either through subscription arrangements with the relevant issuing entities or by release-date downloads from the websites of the issuing entities. Similarly, professional services are impacted by changes in regulatory requirements and standards. Accordingly, the software system of the present invention automatically notifies affected participating professionals of such regulatory changes, which are obtained through subscription arrangements with the relevant regulatory and standards-setting entities or by notice-date downloads from the websites of such entities.

The present invention enables participating professionals and their clients to communicate, share information, and negotiate and/or create documents relating to the professionals' expertise and services. It enables auto-completion of forms across multiple professional practices and seamless referrals between different professional practices through a process which integrates and audits compliance with applicable requirements of informed consent and confidentiality. It opens a communication channel, including live chat, between the professionals and their clients and generates an immutable audit trail of ensuing transactions and interactions. The system also provides for the simplification and clarifications of terminology via these communications by providing simple definitions for particular terms with which an end user is not familiar.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope of the foregoing summary description.

BRIEF DESCRIPTION OF THE DRAWINGS

FIG. 8 is an exemplary wireframe for a lawyer's professional home screen in one embodiment of the Professional App of the present invention;

FIGS. 16A-16C are exemplary wireframes for the authentication of study participants and professionals according to one embodiment of the Web App of the present invention;

FIGS. 17A-17B depict an exemplary information architecture for an exemplary Studies Menu tailored for clinical trials of new pharmaceutical products;

FIGS. 18A-18C depict exemplary wireframes corresponding to the Q&A component of the exemplary Studies Menu tailored for clinical trials of new pharmaceutical products;

FIGS. 20A-20E depict exemplary wireframes corresponding to the Documents component of the exemplary Studies Menu tailored for clinical trials of new pharmaceutical products;

FIGS. 21A-21B depict exemplary wireframes corresponding to the Settings component of the exemplary Studies Menu tailored for clinical trials of new pharmaceutical products; and FIGS. 22A-22E depict exemplary wireframes corresponding to the Study Management component of the exemplary Studies Menu tailored for clinical trials of new pharmaceutical products.

DETAILED DESCRIPTION OF THE PREFERRED EMBODIMENT

Figure 2:
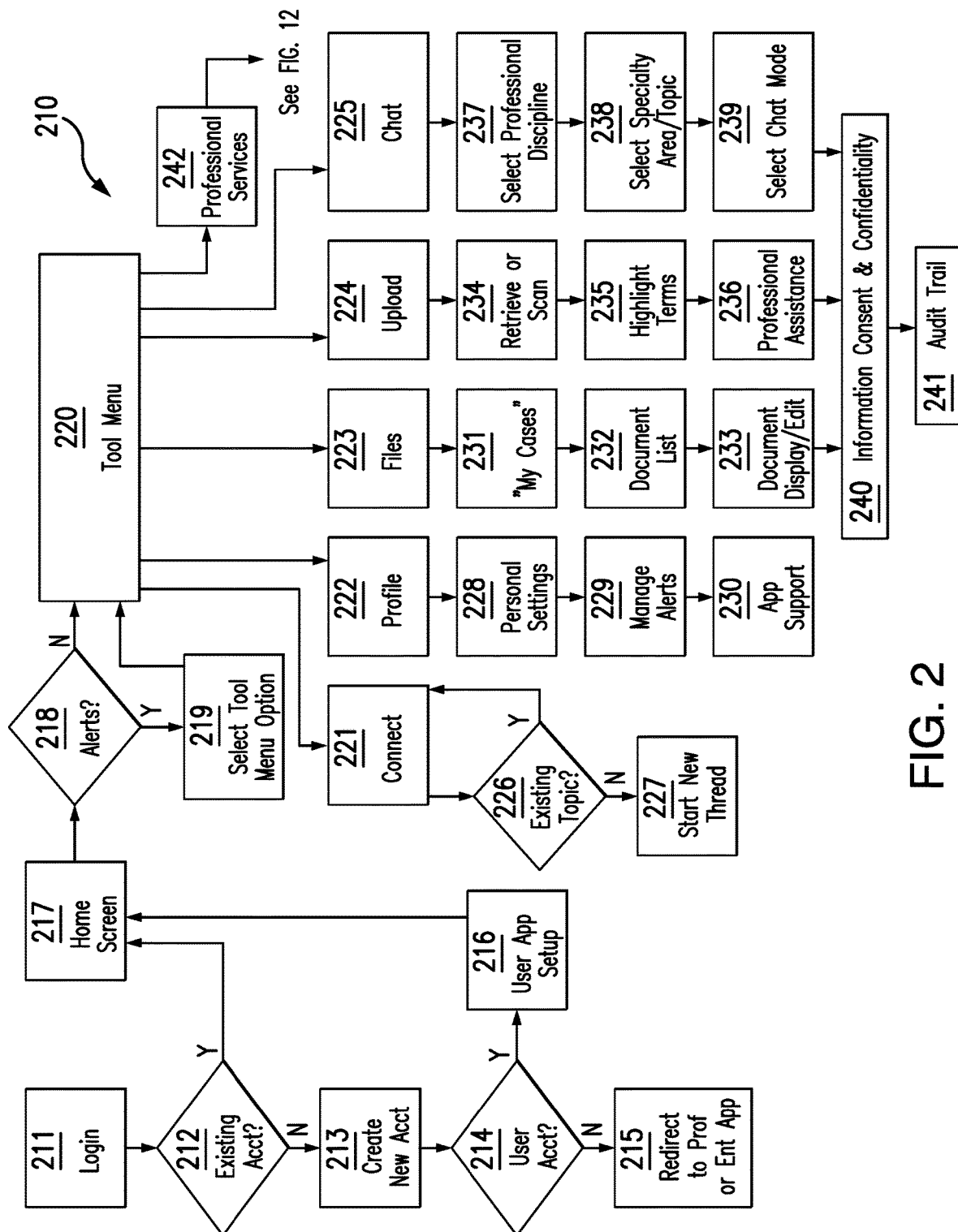
FIG. 2 is an exemplary flow chart of one embodiment of the User App of the present invention.

Referring to FIG. 2, an exemplary flow chart for one embodiment of the User App 210 is depicted. In the Login screen 211, the standard user logs in with a username and password, if the user has an existing account 212. If not, the user creates a new account 213 214, he/she is guided through setup 216 of the User App 210. Professionals and enterprise users are redirected 215 to the Professional App 310 and the Web App 410, respectively.

Figures 5A, 5B:
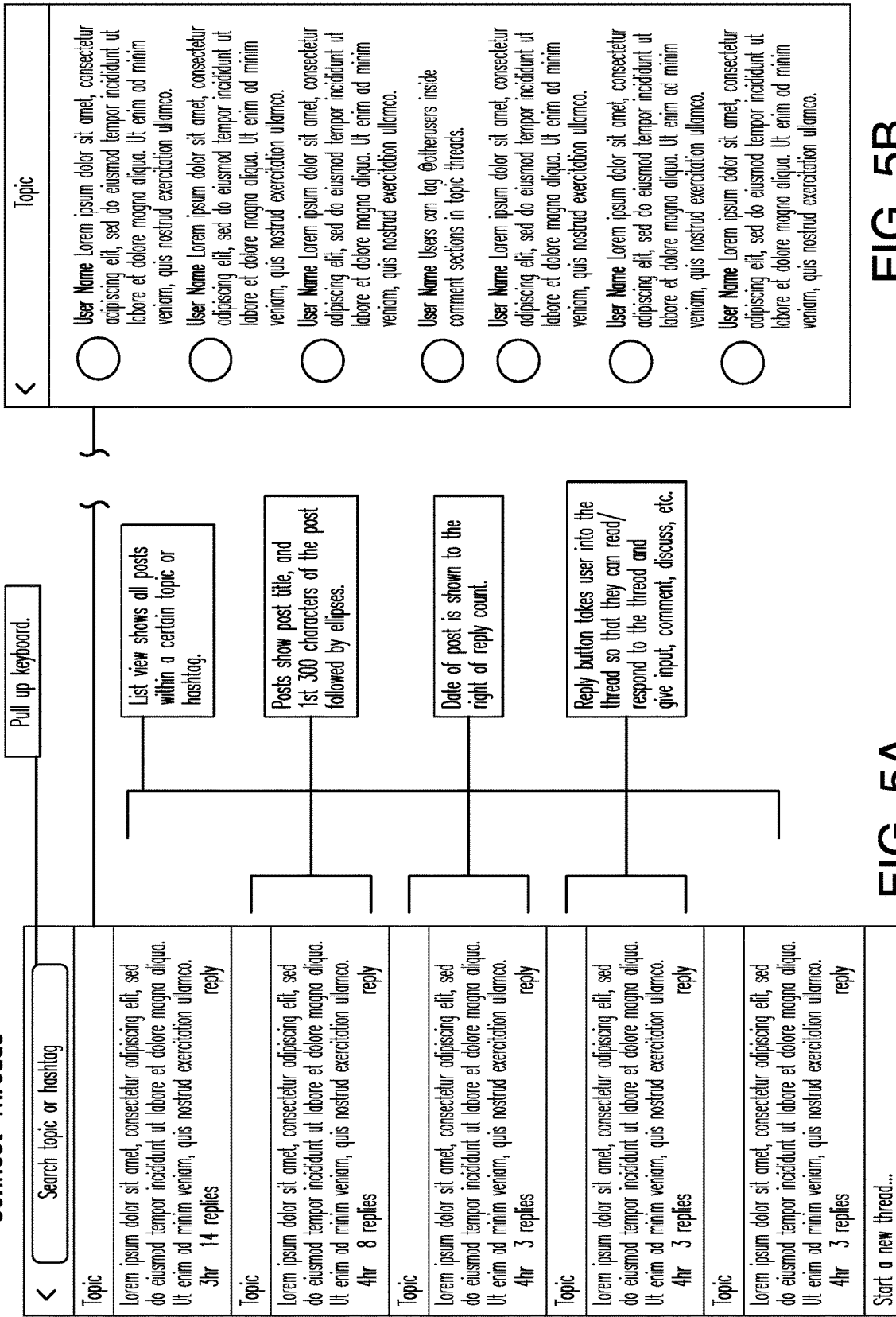
FIGS. 5A & 5B are exemplary wireframes for the "Connect Threads" screens of one embodiment of the User App of the present invention.
Figure 6A:
FIGS. 6A-6D are exemplary wire frames for the "My Cases" screens of one embodiment of the User App of the present invention.
Figures 6B, 6C, 6D:

Upon login 211 to an established account 212 216, the User App 210 opens the Home Screen 217, which defaults to a display of any "Connect" 221 chats that the user has opened or participated in. If the user has any alerts requiring action 218, he/she will select the appropriate option 219 from the User's Tool Menu 220 to deal with it. If not, clicking on the "Connect" button 221 directs the user to an itemized list of topics 226 being discussed by other standard or enterprise users. Users can search by topic or hashtag for existing topic discussions via a search bar at the top of the page. Exemplary wireframes for these "Connect Threads" screens are depicted in FIGS. 5A and 5B. Users can start a new thread 227 by tapping the "Start a new thread" at the bottom of the screen.

Through the Profile tab 222, users manage their personal settings 228 and alerts 229. Here they can toggle alerts from "Connect" 221, "My Cases" 231 and "Chat" 225 on and off. And here they can also access User App Support 230, to report problems or upgrade/downgrade their account.

Under the Files option 223, users can look up "My Cases" 231 to view legal documents they have signed or need to sign, as well as private group chats to which they have been invited by an enterprise user. Legal documents are displayed in an itemized list 232 identifying the issuing business name and the date when the document was sent to the user. Upon clicking on any document on the list 232, the user displays the full document 233 and can highlight terms within the document for definition or open a live chat with a professional, such as a lawyer. If the document requires his/her signature, the user can agree to the document by VoIP recording, touch screen signature, or one touch confirmation. Exemplary wireframes for these "My Cases" screens are depicted in FIGS. 6A-6D.

Using the Upload option 224, users can upload scanned or saved files and documents 234. The User App provides OCR to convert scanned images into readable text. When a user highlights terms in a document 235, the App pulls definitions from search engines, websites and/or databases and displays them. The definition display allows the user to elect a "depth" of definition of the subject terminology, ranging from a brief dictionary-type definition to an expanded analysis of the terminology with examples of its usage. Optionally, the definition display can include an audible narration component explaining the terminology and/or an animation figure or character giving an audible explanation of the terminology. Users can also highlight sections of a document to refer to while requesting the assistance of a professional 236, such as a lawyer, through the App's Chat feature 225.

Figure 7B:
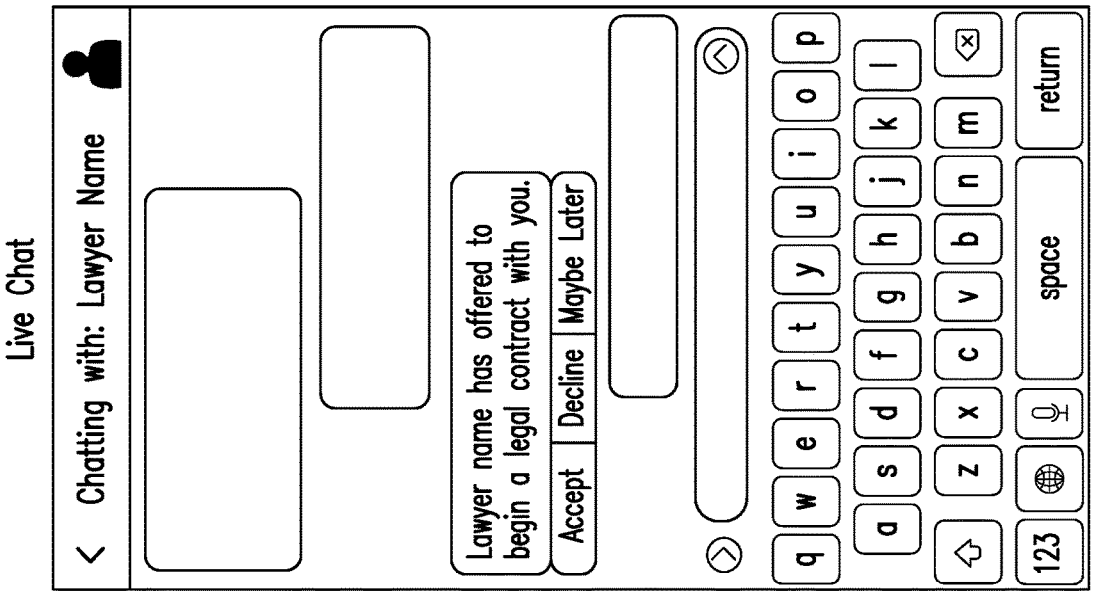
FIGS. 7A & 7B are exemplary wireframes for "Live Chat" screens of one embodiment of the User App of the present invention.
Figure 7A:
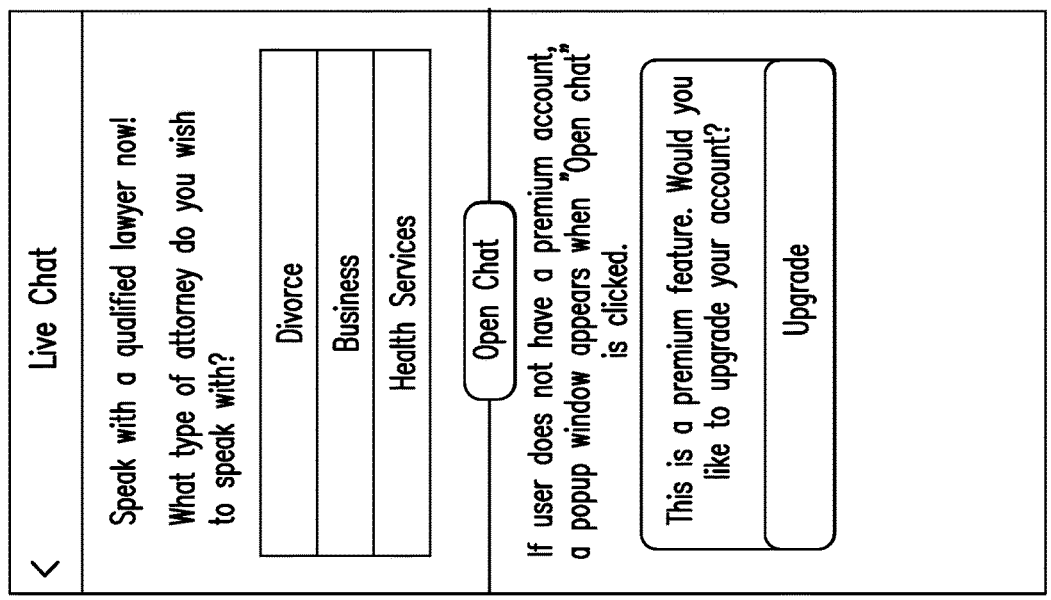

Through the Chat feature 225 of the User App 210, users can open a live chat with a qualified professional. The user selects a professional discipline 237, such as law, and then selects a specialty area or topic 238 from a list of categories. The user and/or professional can select a chat mode 239 of text, VoIP call or video chat. Exemplary wireframes for "Live Chat" screens specific to a lawyer are depicted in FIGS. 7A and 7B. With respect to shared user information and communications in the Files 223, Upload 224 and Chat 225 operations, the User App 210 informs the user of his/her privacy rights and records the user's informed consent 240 in an immutable audit trail 241.

Figure 3:
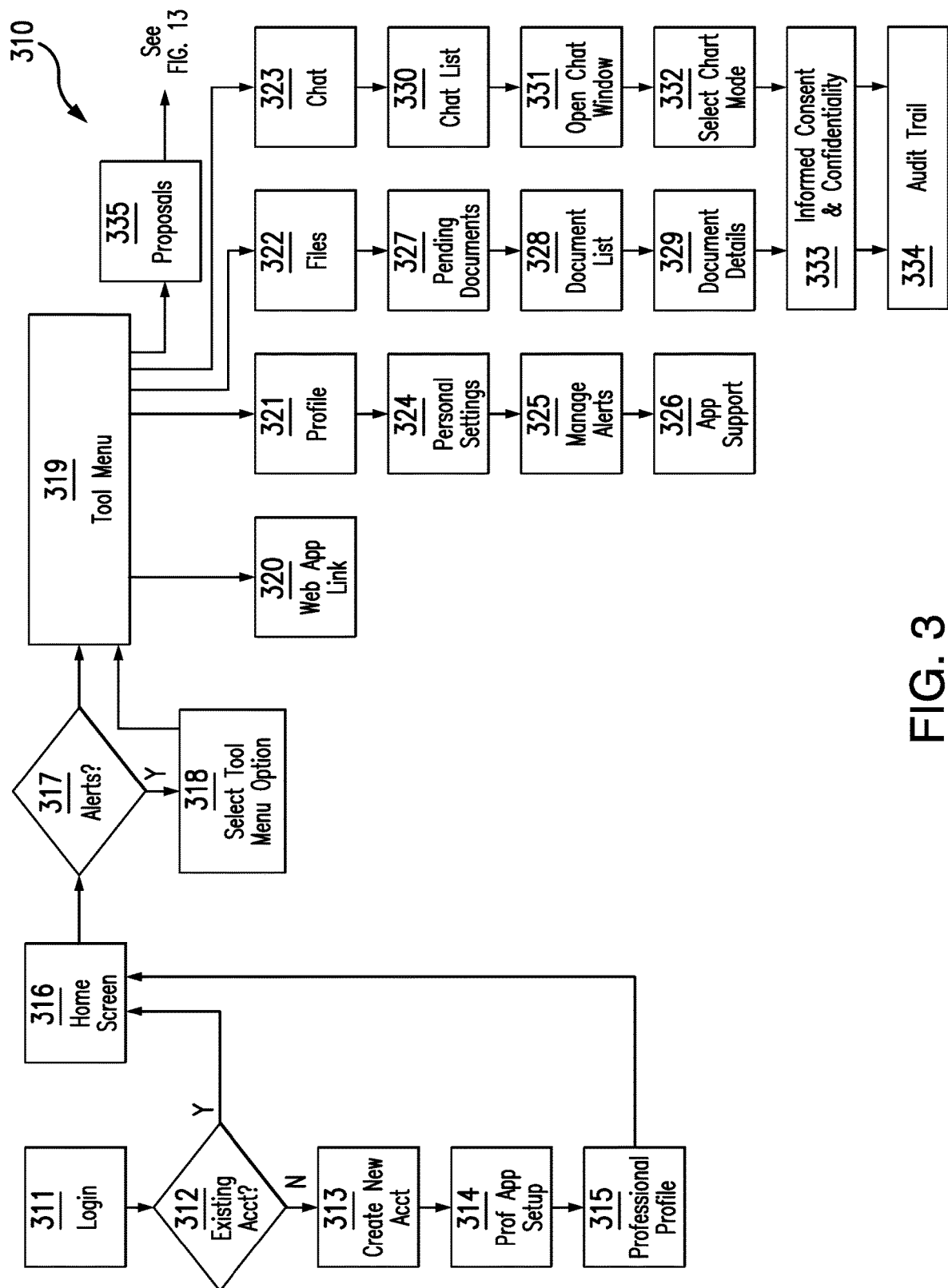
FIG. 3 is an exemplary flow chart of one embodiment of the Professional App of the present invention.
Figure 8:
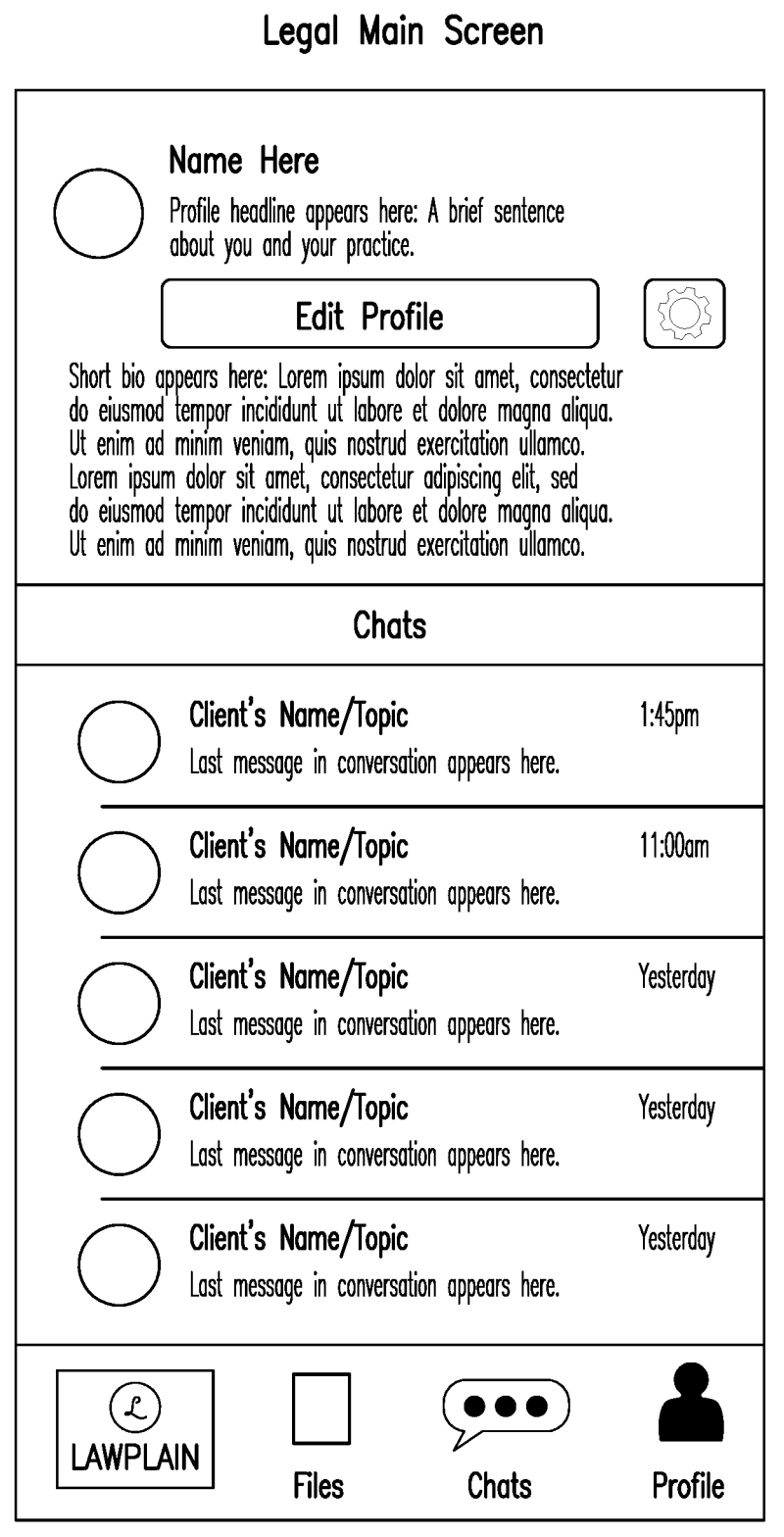

Referring to FIG. 3, an exemplary flow chart for one embodiment of the Professional App 310 is depicted. From the Login screen 311, the professional with an existing account 312 logs in with a username and password. Otherwise, a new account is created 313, and the professional is guided through App Setup 314, in which profile 315 and billing information is supplied and terms of service agreed upon. In either case, after Login 311 the App 310 opens a Home Screen 316, which initially displays an itemized list of the professional's chats, with the most recent appearing first. An exemplary wireframe for a lawyer's professional Home Screen is depicted in FIG. 8.

At the bottom of the Home Screen appears the Professional's "Tool Menu" 319, which includes links to the Web App 320, Profile 321, Files 322, Chat 323, and Proposals 335. If the professional has any alerts requiring action 317, he/she will select the appropriate option 318 from the Tool Menu 319.

Through the Profile tab 321, professionals manage their personal settings 324 and alerts 325. Here they can toggle alerts from "Chat" on and off. These alerts comprise new events that arise in one of their chats, including new chat requests that fall within their area of professional expertise, new messages from existing clients/patients, and VoIP or video chat calling alerts involving existing clients/patients. And here they can also access Professional App Support 326, to report problems or upgrade/downgrade their account.

Under the Files option 322, professionals can upload legal documents 327, such as attorney retainer agreements which they have extended to standard or enterprise users who want to contract for their services. They can display an itemized list of time-stamped documents 328, indicating which have been agreed upon by clients/patients and which are still pending. Upon clicking upon a listed document, full documents details are displayed 329. Professionals can toggle between "agreed" and "pending" to view users who have agreed or not to that document. They can also click on "pending" to send reminders to users who have not yet agreed to the document.

Through the "Chat" line 323 on the Home Screen 316, the professional views an itemized list 330 of chats they have open with standard and enterprise users. The list 330 shows the user's name and chat topic, along with the first 25 characters of the last message and a time stamp of when the message was sent. Clicking on one of these chats allows the professional to open a chat window 331 with the user. The professional and/or the user can select a chat mode 332 of text, VoIP call or video chat. With respect to shared user information and communications in the File and Chat operations, the Professional App informs the user of his/her confidentiality rights and records the user's informed consent 333 in an immutable audit trail 334.

The information exchanged and documented in the "Files" and "Chat" section of the App 310 are private and visible only to the following parties through the following channels:

1. End User. The end user's files are only visible to their respective account accessed via their User App username and password.
2. Enterprise Account. All legal documents signed by an end user can be viewed/stored by the enterprise account that extended the document for the end user to sign. This includes administrative accounts for that specific enterprise account.
3. Professional. When and end user reaches out for assistance from a professional, they consent to share their personal information and information contained in their respective documents with that professional.
4. Group Chats. Group chats are opened only by an enterprise account. Only other enterprise accounts, professionals and standard users invited by the initiating enterprise account can view and access these group chats. Invited parties must sign an NDA or equivalent uploaded by the initiating enterprise account prior to joining the group chat. Within this group chat, documents can be shared from the initiating enterprise account with the members within the group chat.

Figure 4:
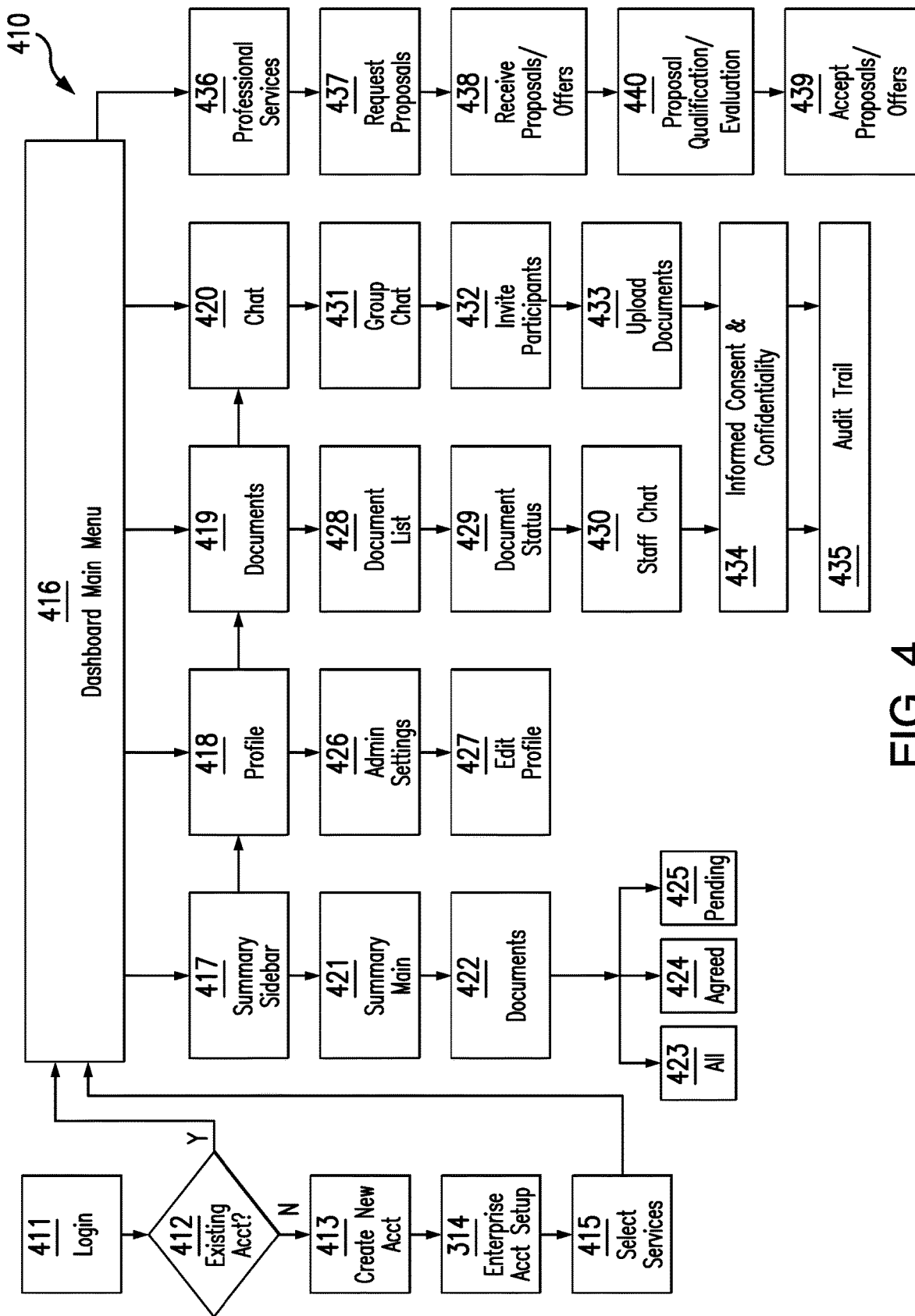
FIG. 4 is an exemplary flow chart of one embodiment of the Web App of the present invention.

Referring to FIG. 4, an exemplary flow chart for one embodiment of the Web App 410 is depicted. The Login 411 procedures for existing accounts 412 and new account creation 413 are followed, and an enterprise account is Setup 414, with selection of services 415 and billing information.

After Login, the App opens to Dashboard Main Menu 416, with links to the Summary Sidebar 417, Profile 418, Documents 419, Chat 420, and Professional Services 436. The Summary Sidebar 417 provides alerts from plan staff regarding potential problems with an enterprise user's current legal documents. The Summary Main Dashboard 421 shows all documents 422 sent to standard users for signing, broken down into three categories: (1) "All" 423, listed with newest first and showing document name, date sent, username of recipient, and whether the user has agreed to the document; (2) "Agreed" 424, showing only signed documents, with the newest listed first; and (3) "Pending" 425, showing only documents that have been sent to the end user but not signed.

Enterprise users can click on the username to display the document name, the full document, the user's digital signature, a saved VoIP agreement, or a verified one tap agreement. Each of these will display as red prompts if the client has not signed the document via that channel.

From the Profile submenu 418, the enterprise account can manage its administrator settings 426 and edit its profile information 427.

Figure 9A:
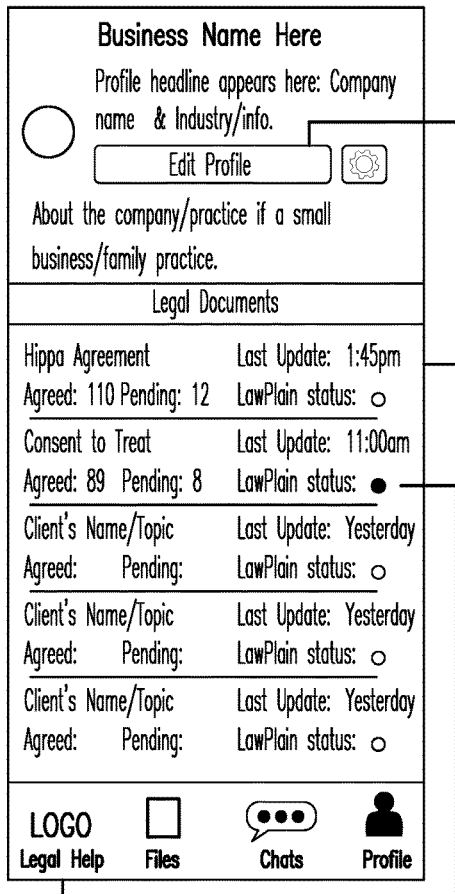
FIGS. 9A-9C are exemplary wireframes for enterprise "Document" screens in one embodiment of the Web App of the present invention.
Figure 9B:
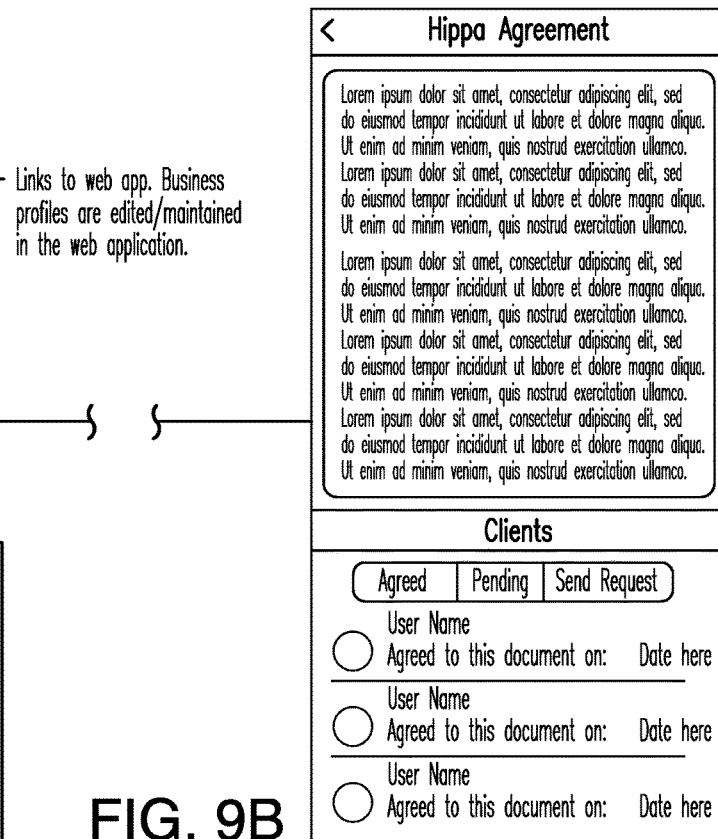
Figure 9C:
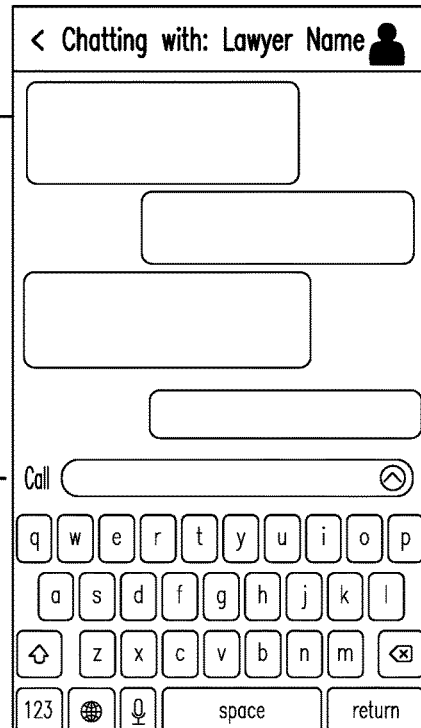

The Documents submenu 419 provides a list of all documents 428 uploaded by the enterprise user to be sent to standard users engaged by the enterprise. The document list displays the document name, upload date and plan status 429. A green indicia indicates that plan staff have reviewed a legal document and found it sufficient to be issued to a standard user engaged by the enterprise account. "Action Needed" indicates that legal issues exist with the document and that a plan lawyer should be consulted. Clicking on the document will populate the Main Dashboard 416 with the complete document so that it can be viewed. From the Dashboard 416, live chats with plan staff 430 and/or staff lawyers can be opened. Exemplary wireframes for enterprise "Document" screens are depicted in FIG. 9A-C.

Figure 10:
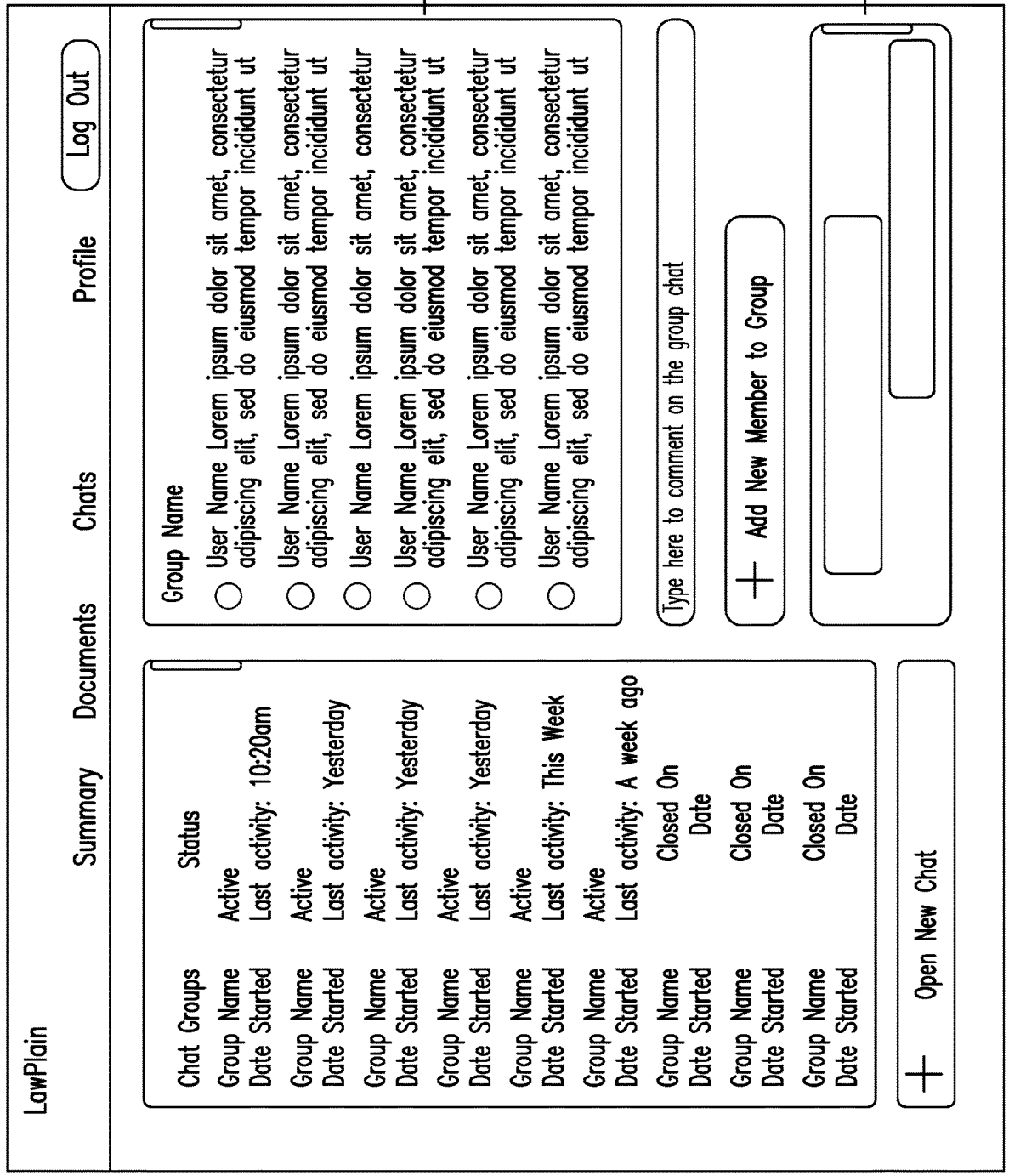
FIG. 10 is an exemplary wireframe for an enterprise "Group Chat" screen in one embodiment of the Web App of the present invention.

The Chats submenu 420 provides an itemized list of group chats 431 opened by the enterprise account. For each group chat, the App displays the group name, start date, time stamp for most recent activity, and active/inactive status. When a group chat is clicked, the full chat opens in the Main Dashboard 416. Comments are displayed in chronological order, and a text field enables the enterprise account to participate in the chat. The enterprise account can engage plan staff in one-on-one chat regarding the group chat. The enterprise account can add new participants 432 to the group chat and can upload legal documents 433 to the entire group. The App enables user selection of alternate group chat 431 modes comprising text, VOIP or video chat. An exemplary wireframe for an enterprise "Group Chat" screen is depicted in FIG. 10.

With respect to shared user information and communications in the Document and Chat operations, the Enterprise App informs the user of his/her privacy and confidentiality rights and records the user's informed consent and NDA agreements 434 in an immutable audit trail 435.

Figure 11:
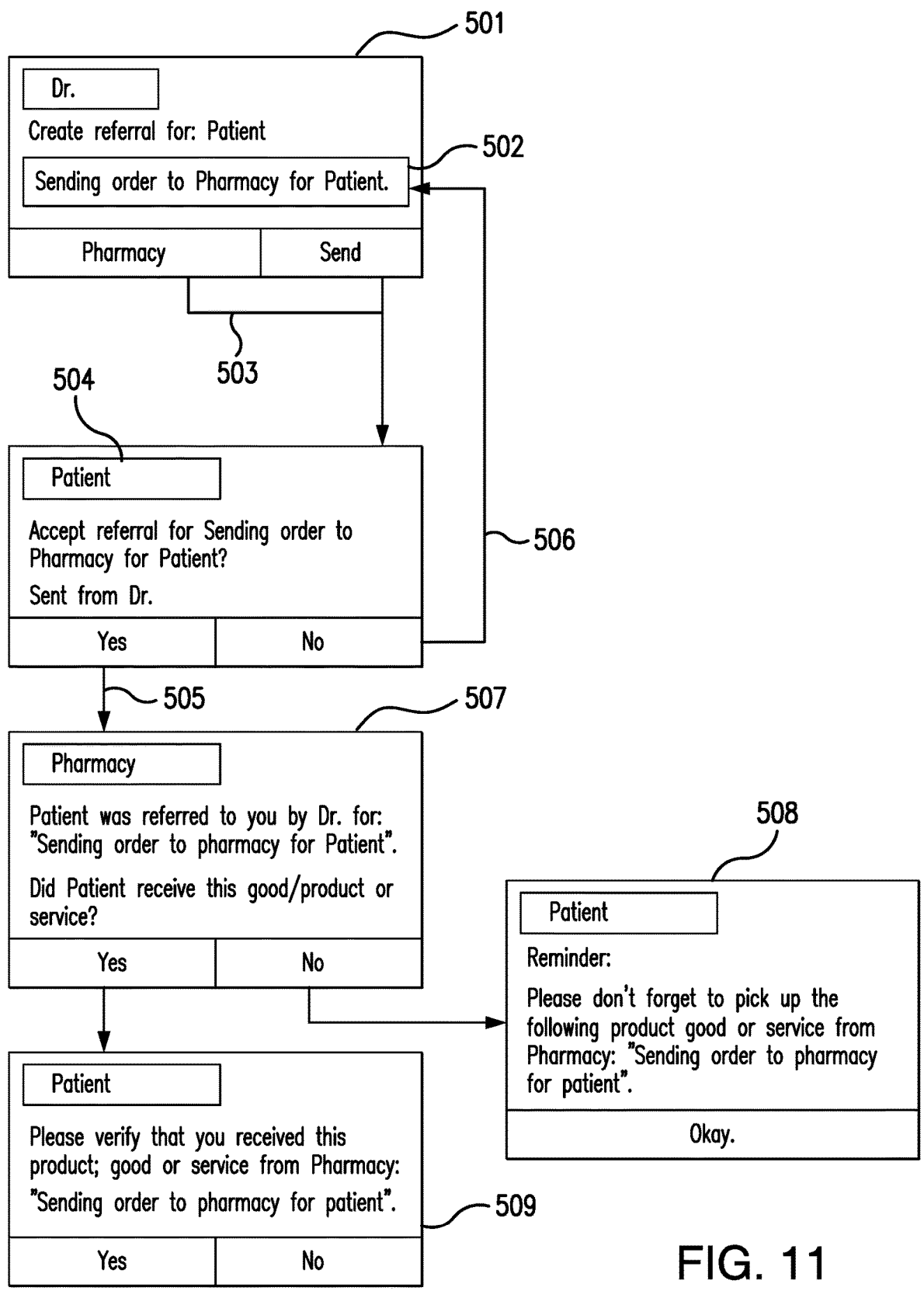
FIG. 11 is an exemplary flowchart of wireframes for enterprise-to-enterprise referral screens in one embodiment of the Web App of the present invention.

As shown on FIG. 11, the Web App also enables referrals from one enterprise account to another. In this instance, a medical practice is referring a patient to a pharmacy business. In the first screen 501, a text box 502 is provided for the referring medical enterprise to describe the purpose of the referral. A search bar 503 allows the referring enterprise to search for a pharmacy enterprise to which to refer the patient. The second screen 504 notifies the patient of the proposed referral and elicits the patient's consent 505. If the patient declines the referral 506, the referring medical practice can propose another pharmacy referral. If the patient accepts, the pharmacy is notified 507, and verifies whether or not the patient has received the product or service 508 509. The process audits and records the patient's consent to the referral as well as their satisfaction with the services provided by the referred business.

Figures 12, 13:
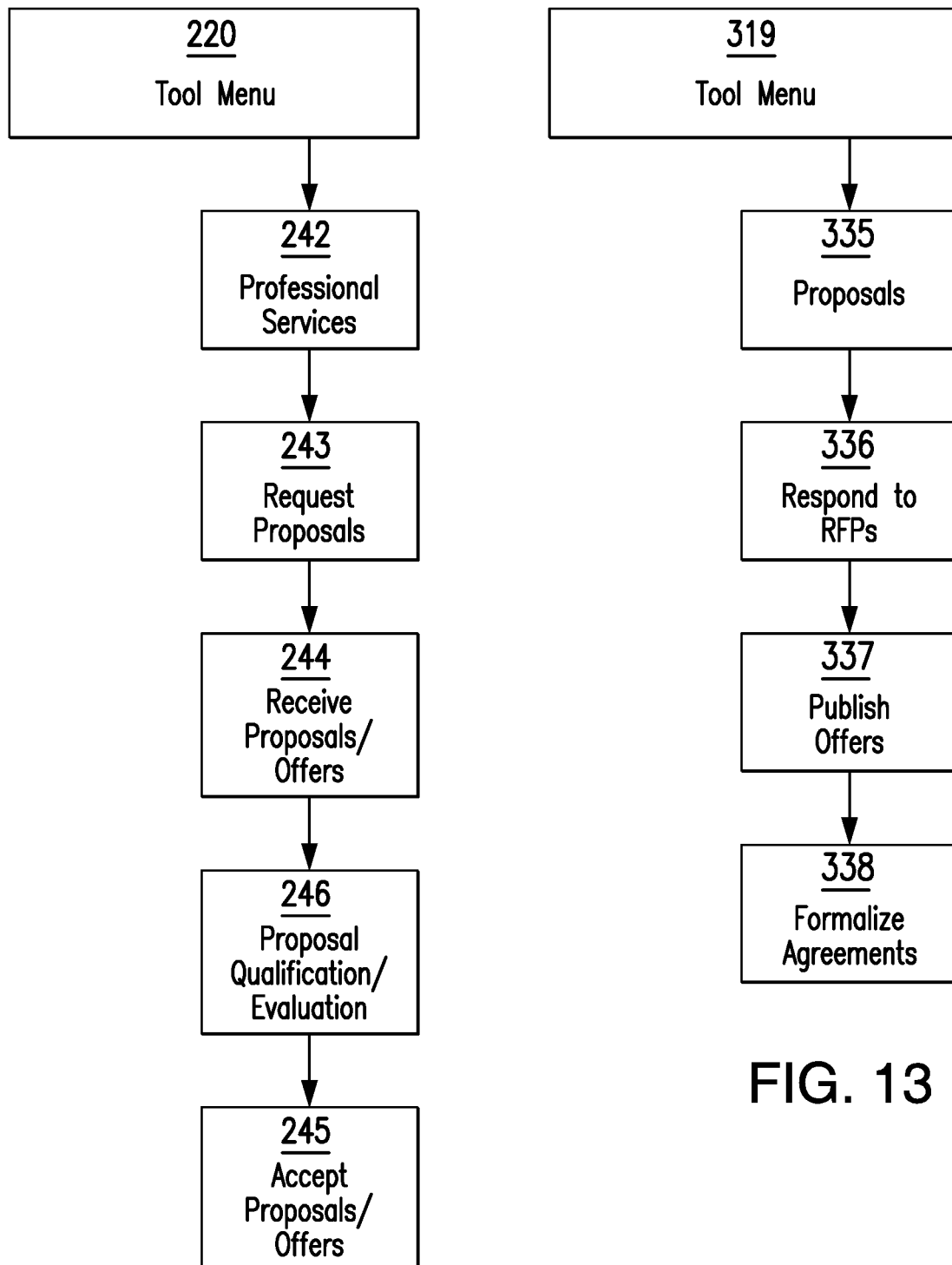
FIG. 12 is an exemplary detail of the User App flowchart of FIG. 2, showing the "Professional Services" submenu.
FIG. 13 is an exemplary detail of the Professional App flowchart of FIG. 3, showing the "Proposals" submenu.

Referring to FIGS. 2, 4, and 12, exemplary embodiments of the User App 210 and the Web App 410 feature a Professional Services submenu 242 436 under the Tool Menu 220 and the Dashboard Main Menu 416, respectively.

Using these tabs, a standard user or enterprise user specifies the professional services 242 436 for which proposals are sought 243 437. Referring to FIGS. 3 and 13, the Professional App features a Proposals submenu 335 under the Tools Menu 319, through which participating professionals respond to requests for proposals 336 with responsive proposals, which are received by the originating User App 244 or Web App 438, where the proposals can be accepted 245 439.

Alternatively, participating professionals can use the Professional App 310 to initiate offers for specified professional services at specified fees 337, which offers 337 are received by standard users 244 with the User App 210 or by enterprise users 438 with the Web App 410. When such a professional offer 337 is accepted by a user 245 439, the professional proceeds through the submenus to formalize a professional services agreement 338.

For example, a standard user who is building a new home could solicit fixed-fee proposals from architects to design the home to certain specifications and could also solicit fixed-fee proposals from attorneys to draft the architectural services contract. The standard user could also accept a published fixed-fee offer by an engineering enterprise user to design and install a septic system for the new home.

In the User App 210 and the Web App 410, the respective Professional Services submenus 242 436 also include a Proposal Qualification/Evaluation option 246 440. The Proposal Qualification/Evaluation option 246 440 allows a standard user or an enterprise user to define minimum qualifications for professionals who want to submit fixed-fee proposals for the specified services. For example, a standard user seeking fixed-fee proposals from attorneys to represent the user in a divorce case could stipulate that proposals only be accepted from only certified civil trial attorneys. The App software will then apply the stipulated qualifications to generate a "short list" of qualifying proposals.

The Proposal Qualification/Evaluation option 246 440 also allows a standard user or enterprise user to establish multiple criteria for evaluating professional services proposals. Using such evaluation criteria, the App software will then rank the proposals based on the evaluation criteria. For example, the standard user seeking a divorce trial attorney could define evaluation criteria such as: five or more years of trial experience, at least ten fully litigated cases, and membership in the family law section of the state bar association. The App software will then assign to each proposal a "grade" of 0 through 3 based on compliance with the foregoing criteria.

Figure 14:
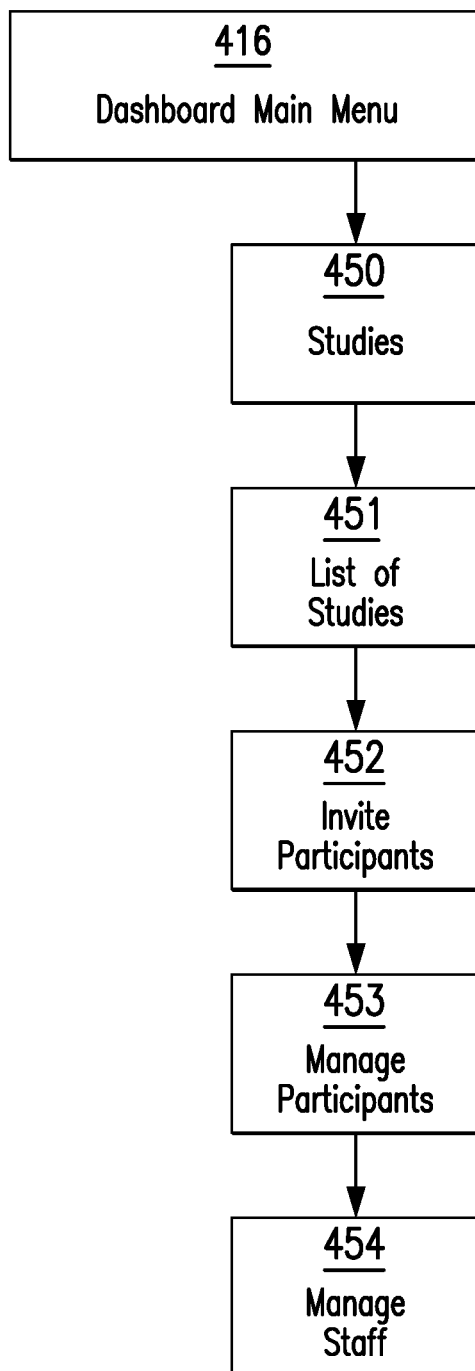
FIG. 14 is an exemplary detail of the Web App flowchart of FIG. 4, showing the "Studies" submenu.

In some embodiments, the Web App 410 can also include a Studies submenu 450 under the Dashboard Main Menu 416, as depicted in FIG. 14. Under the Studies submenu 450, an enterprise user can manage a range of technical, research (including academic and medical), and/or clinical studies, such as testing of a new product or clinical trials of a new pharmaceutical.

Figure 15C:
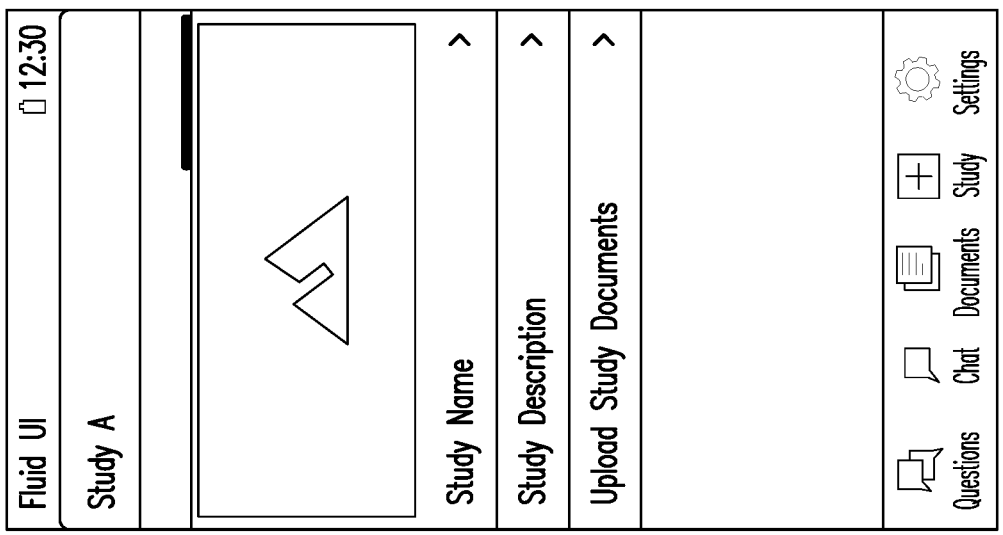
FIGS. 15A-15C are exemplary wireframes for the "Study Management" screens of one embodiment of the Web App of the present invention.
Figure 15B:
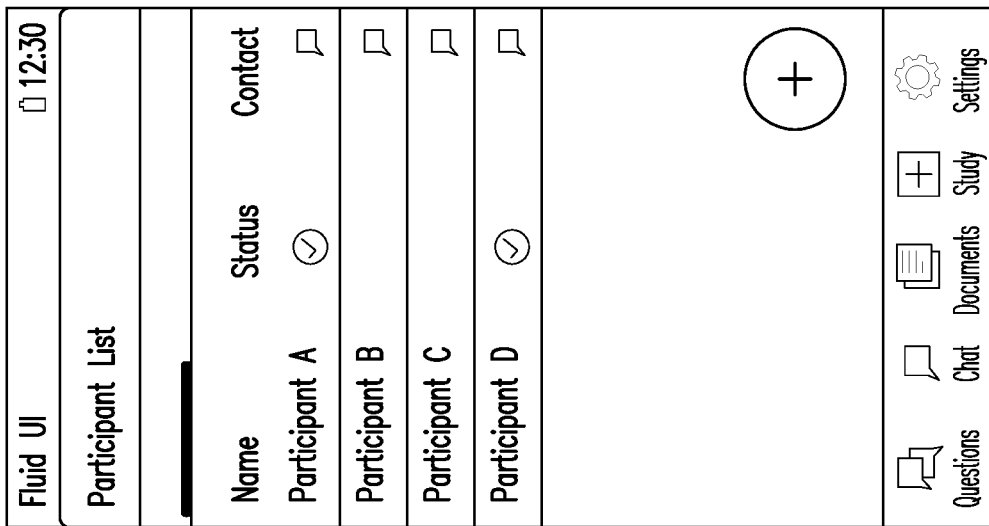
Figure 15A:
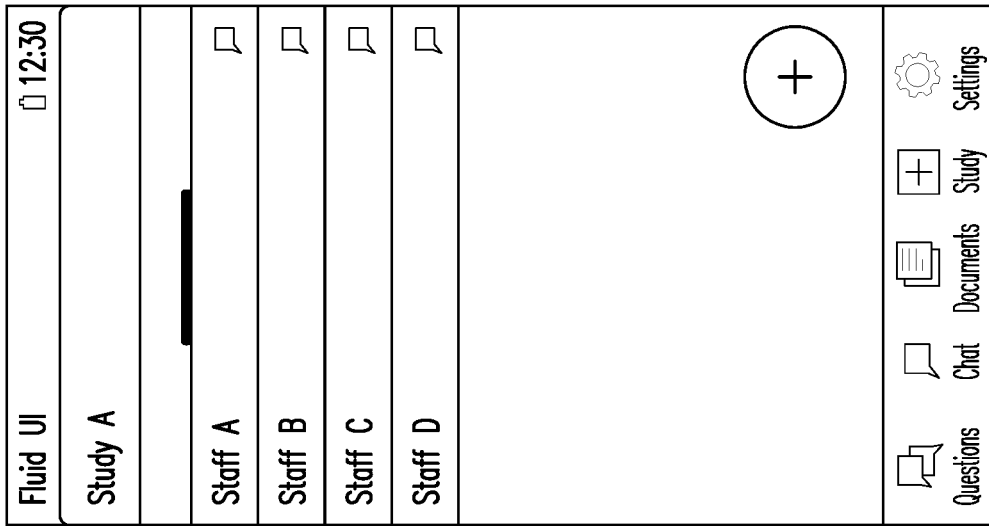

Under the Studies submenu 450, the enterprise user has access to a list of ongoing studies 451, invites participants to the studies 452, and manages participants 453 and staff 454 associated with the studies. For example, through the management of participants, the enterprise can track and record compliance with clinical/research guidelines so to reduce the risk of liability arising from non-compliant participants. Exemplary wireframes for study management are depicted in FIGS. 15A-C.

Exemplary authentication wireframes for study participants and professionals are shown in FIGS. 16A-C. The authentication process can also include password-protected permissions for access to study data and documents, depending on the role of the participant, staff or professional involved. Such permissions can allow designated staff and/or professionals to review data and draft reports relating to the studies and to edit draft documents, depending on the level of permissions.

In the case of studies subject to regulatory review and standards, such as FDA drug approvals, the software automatically associates the requisite documents and forms with each study category and automatically updates the documents and forms to the latest versions.

As authorized by the supervisor of the enterprise account, the Chat submenu 420 of the Web App 410 can be used for communications between study staff, supervisors, professionals and/or participants. The Chat 420 system can be used to track activities of staff and participants, obtain and document required consents 434 and provide audited risk management 435.

Optionally, the Studies submenu 450 can be particularly tailored to the requirements of certain enterprise uses, subject to a commensurate fee.

Figures 18A, 18B, 18C:
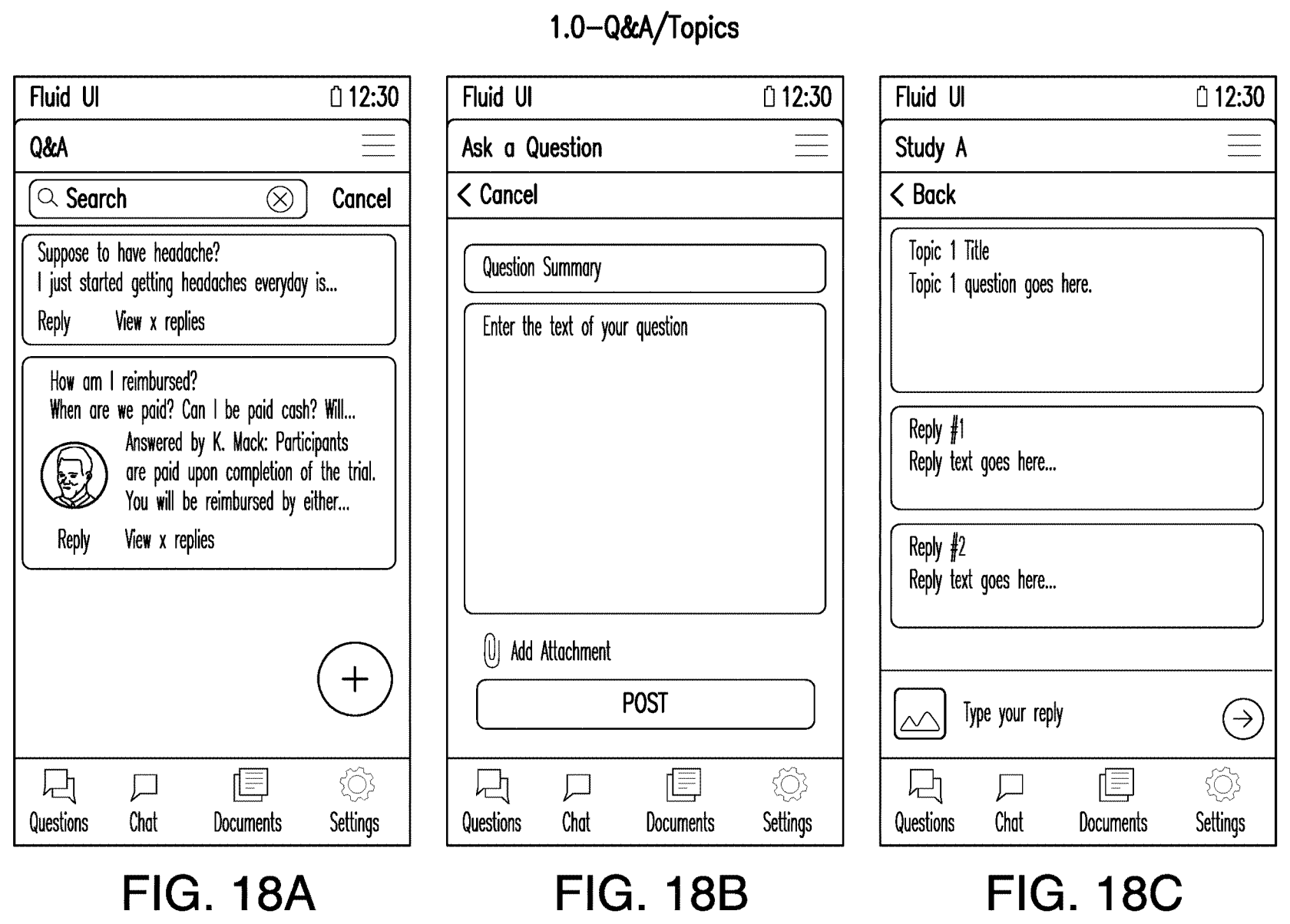

FIGS. 17A-17B display an exemplary information architecture for a Studies menu tailored to clinical trials of new pharmaceutical products. Corresponding exemplary wireframes for each information component are depicted in FIGS. 18A-18C, for Q&A, FIGS. 19A-19C, for Messaging, FIGS. 20A-20E for Documents, FIGS. 21A-21B for Settings, and FIGS. 22A-22E for Study Management.

Figure 19A:
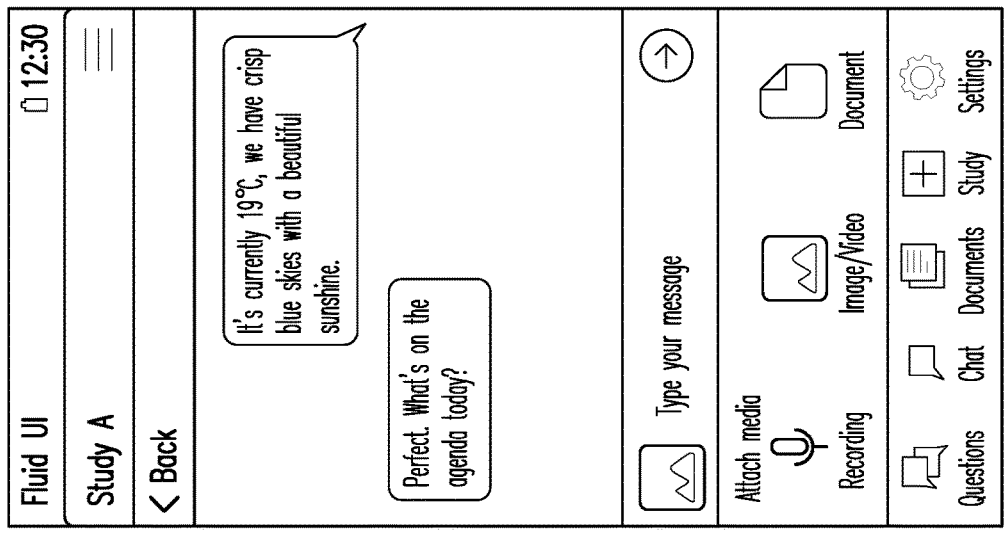
FIGS. 19A-19C depict exemplary wireframes corresponding to the Messaging component of the exemplary Studies Menu tailored for clinical trials of new pharmaceutical products.
Figure 19B:
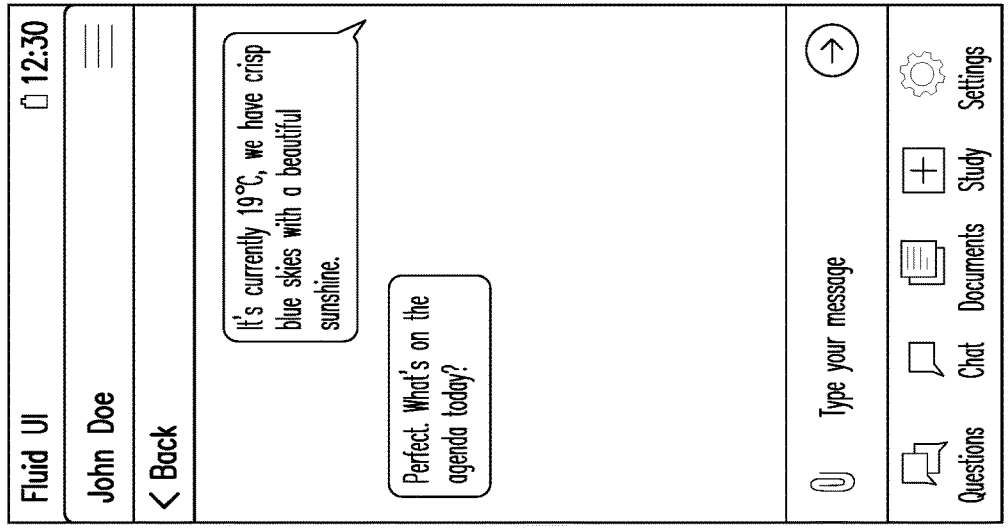
Figure 19C:
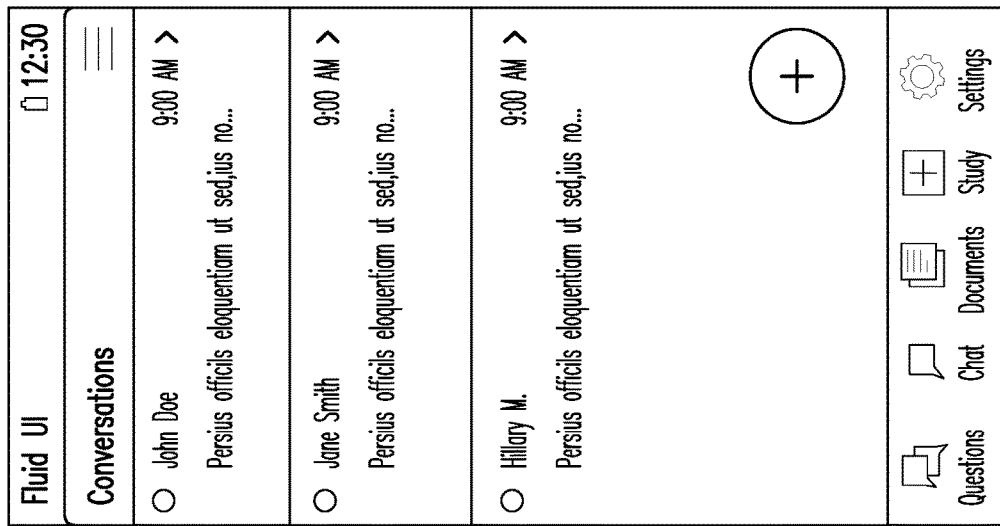
Figure 20A:
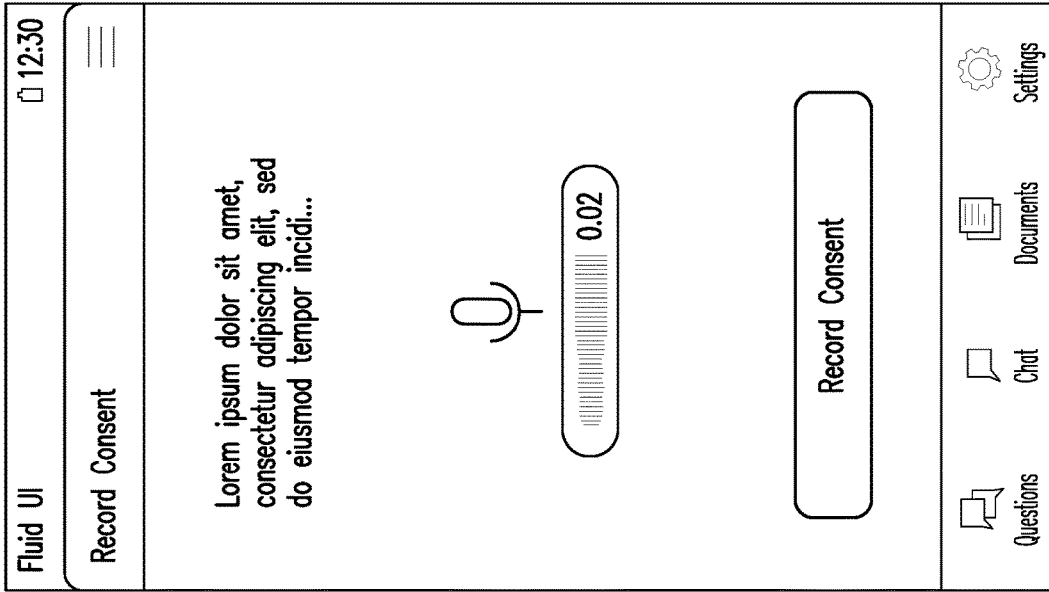
Figure 20B:
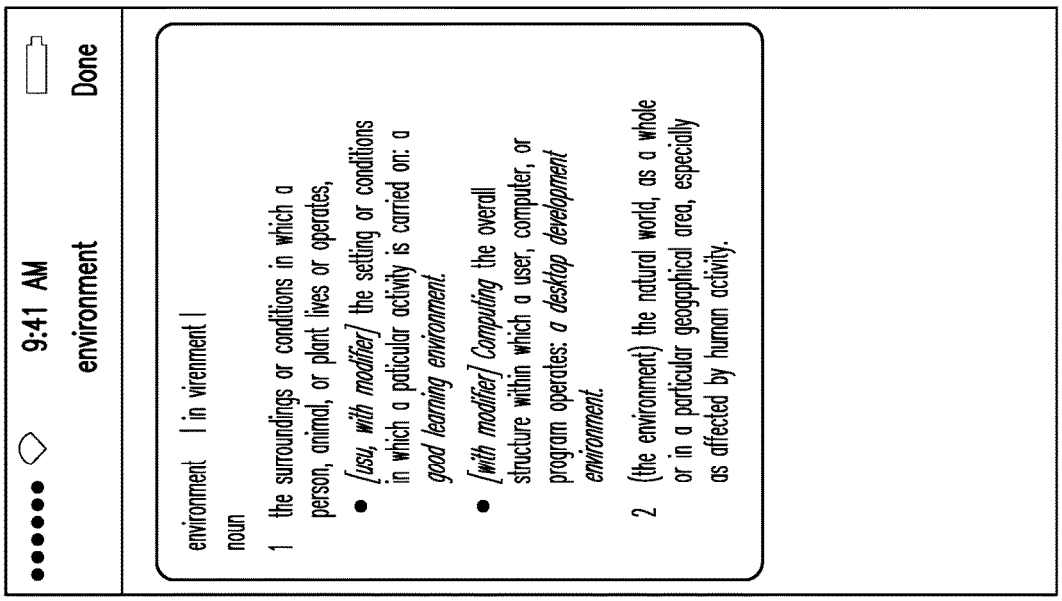
Figures 20C, 20D, 20E:
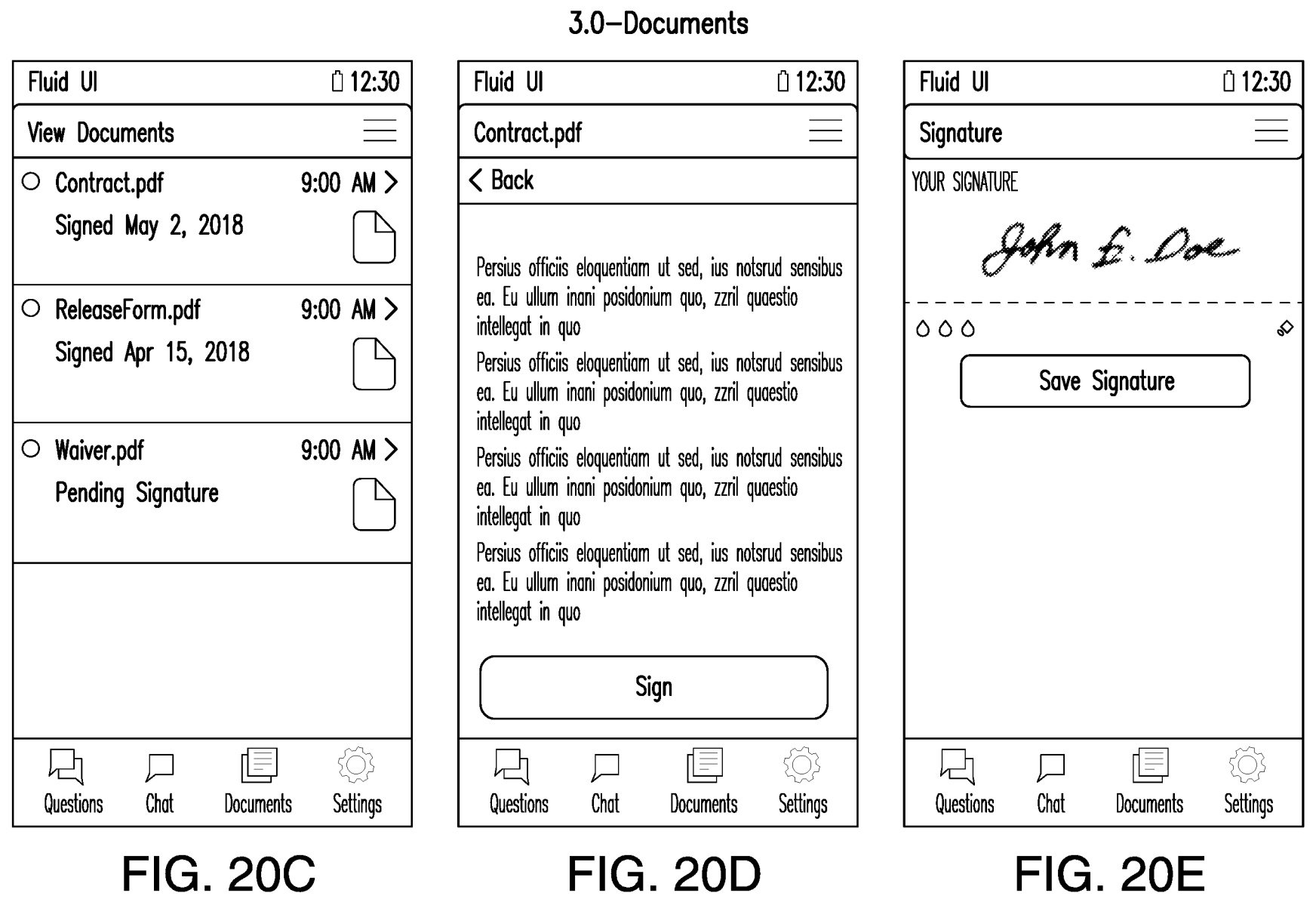

Referring to the foregoing figures, a supervisor of the clinical trials can invite a standard user to be a participant in the trials, as shown in FIG. 22E, the supervisor and can require a recorded consent from the participant, as shown in FIG. 20B and FIG. 22D. The supervisor can edit study settings to specify allowed communications between participants, as shown in FIG. 19A, and can upload documents to participants, including consent forms and instructions, as shown in FIG. 20B and FIG. 20C. Under the Study Management functions, the supervisor can track the activities of clinical trial participants and staff, as shown in FIGS. 22A-22C.

Supervisors, participants and staff can view a list of all clinical trials they are involved in. Supervisors can select, add or replace staff in each of their active clinical trials. The App will provide instructions to executives of the sponsoring pharmaceutical enterprise regarding selection of supervisors, staff and professionals for the clinical trial team, based on their credentials and assignment of roles in the team. Once the team members are selected, their profiles are uploaded to the App and can be viewed by authorized team members. The App gives the team members specific instructions as to how to conduct their respective tasks in the clinical trial. The clinical data is collected by the App and securely stored in the System Database, with access based on team member permissions.

Figure 1:
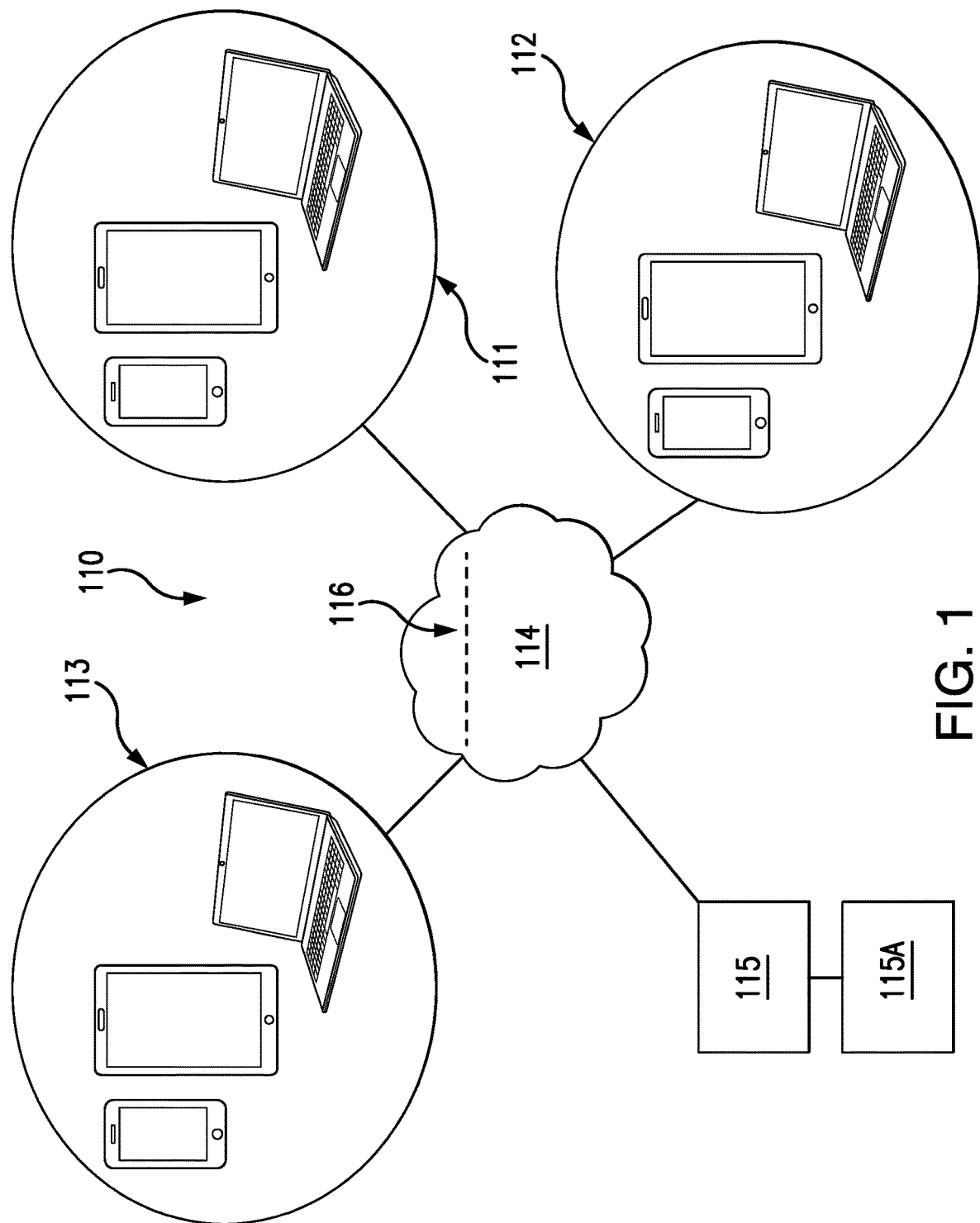
FIG. 1 is a schematic diagram of the hardware and network architecture of the present invention.

The present invention assures that the most current versions of professional forms are always in use on its platform. Forms associated with professional services are automatically updated as of the release date of new form versions. This is done either by subscription arrangements with the relevant form-issuing entities, or by release-date downloads from their public websites. For example, a participating medical professional would automatically be supplied with the latest versions of HIPAA forms sent by the System Server 111 (FIG. 1) to the Professional App 310, based on subscription services with state medical regulatory agencies.

The system of present invention also assures that its participating professionals are promptly notified of any changes in regulations or standards affecting the services they render to standard and enterprise users. The system software receives notices of all relevant changes in regulations and standards through subscription arrangements with regulatory and standards-setting entities or by notice-date downloads from their public websites. For example, a participating physician who has been consulted by a standard user concerning high blood pressure would receive notices regarding FDA approvals of new blood pressure medications.

Although the foregoing embodiments of the present invention have been disclosed for illustrative purposes, those skilled in the art will appreciate that many additions, modifications and substitutions are possible, without departing from the scope and spirit of the present invention.

What is claimed is:

1. An integrated computerized network system which initiates, mediates, manages, tracks, records and audits multiple network interactions between and among multiple system users, consisting of multiple individual standard users, multiple enterprise users and multiple participating professionals, the network system comprising:
    system software, comprising a system database, a server software, at least one downloadable native User App, for use by the standard users, at least one downloadable native Professional App, for use by the participating professionals, and at least one Web App, for use by the enterprise users, wherein the Professional App links to the Web App;
    system hardware, comprising standard user pc devices, used by the standard users, enterprise pc devices, used by the enterprise users, professional pc devices, used by the participating professionals, and a system server, wherein the user pc devices run the User App, the enterprise pc devices access the Web App, the professional pc devices run the Professional App with a link to the Web App, and the system server runs the server software, and wherein the system hardware is interconnected through an internet;
    wherein the network system enables a private communication linkage between any one of the standard users and any one of the professional users with whom the standard user has established a confidential relationship; and
    wherein the network system uses a blockchain process to record and preserve all interactions between and among the system users in an immutable network audit trail, which is stored in the system database.

2. The network system according to claim 1, wherein the User App enables each of the standard users to upload or download shared user files and shared user documents to or from selected counterparties consisting of one or more of the participating professionals and or alternatively one or more of the enterprise users, and wherein the User App enables each of the standard users to open from within the shared files and the shared documents a live chat with the selected counterparties regarding the shared user files and the shared user documents and or alternatively regarding highlighted sections of the shared user files and the shared user documents which have been selected by the standard user.

3. The network system according to claim 2, wherein the User App alerts each of the standard users to actions required in connection with the shared user files and the shared user documents and enables each of the standard users to view the status of any one or more of the shared user files and the shared user documents and to agree or consent to any one or more of the shared user files and the shared user documents by a voice confirmation, by a touch screen confirmation, or by an electronic signature.

4. The network system according to claim 3, wherein the User App enables each of the standard users to highlight one or more selected terminologies in any one or more of the shared user files and the shared user documents, and wherein the User App displays terminology definitions for each of the selected terminologies, and wherein the User App enables the standard user to select from multiple, progressively expansive levels of definitional depth and to select a definitional medium for each of the selected terminologies.

5. The network system according to claim 4, wherein the Web App enables any one of the enterprise users to upload or download shared web files and shared web documents to or from selected web counterparties, consisting of one or more of the participating professionals, and or alternatively one or more of the standard users, and or alternatively one or more network staff professionals, and wherein the Web App enables the enterprise user to conduct a group live chat among the selected web counterparties regarding the shared web files and the shared web documents and or alternatively regarding highlighted sections of the shared web files and the shared web documents.

6. The network system according to claim 5, wherein the Professional App enables any one of the participating professionals to upload or download shared professional files or shared professional documents to or from selected professional counterparties, consisting of one or more of the participating professionals, and or alternatively one or more of the standard users, and or alternatively one or more of the enterprise users.

7. The network system according to claim 6, wherein the Professional App enables any one of the participating professionals to view the status of any one or more of the shared professional files and the shared professional documents, and wherein the Professional App prompts the participating professional for actions required in connection with the shared professional files and the shared professional documents, and wherein the Professional App enables the participating professional to send messages to or engage in a professional live chat with any one of the selected professional counterparties with respect to actions required in connection with the shared professional files and the shared professional documents.

8. The network system according to claim 7, wherein the User App, the Web App and the Professional App each use a blockchain process to immutably monitor, track, record and audit compliance with requirements pertaining to legal and professional standards, confidentiality, conflicts-of-interest and informed consent, and wherein the network system compiles and stores an immutable compliance audit trail in the system database.

9. The network system according to claim 8, wherein the Professional App automatically updates the shared professional files and the shared professional documents in compliance with relevant changes required by governmental and private regulatory entities, and wherein the Professional App automatically notifies each of the participating professionals of changes in regulatory requirements and standards affecting services performed by the participating professional in connection with the network system.

10. The network system according to claim 9, wherein the Web App enables network referrals of standard users between and among the enterprise users and the participating professionals, and wherein the Web App uses a blockchain process to immutably record and audit informed consent of the standard user to the network referral and satisfaction of the standard user with the network referral, and wherein the network system compiles and stores an immutable referral audit trail in the system database.

11. The network system according to claim 10, wherein the User App and Web App enable any one of the standard users and the enterprise users, respectively, to issue a request for proposal (RFP) from qualified participating professionals for specified professional services, and wherein the Professional App enables the qualified participating professionals to submit professional services proposals in response to the RFP.

12. The network system according to claim 11, wherein the User App and the Web App enable the standard users and the enterprise users, respectively, to define minimum professional qualifications in connection with the RFP, and wherein the User App and the Web App apply the minimum professional qualifications to the submitted professional services proposals to generate a short list of qualifying professional services proposals.

13. The network system according to claim 12, wherein the User App and the Web App enable the standard users and the enterprise users, respectively, to define multiple proposal evaluation criteria for evaluating the qualifying professional services proposals, and wherein the User Ap and the Web App apply the proposal evaluation criteria to rank the qualifying professional services proposals.

14. The network system according to claim 13, wherein the Web App contains a Studies Module, which enables any one of the enterprise users to manage enterprise studies comprising technical, research, academic, medical, pharmaceutical, and or alternatively clinical studies, including new product testing and clinical trials of new pharmaceuticals.

15. The network system according to claim 14, wherein the Studies Module enables the enterprise user to access a list of ongoing enterprise studies, to invite study participants, study staff and study professionals to any one of the enterprise studies, and to manage the study participants, the study staff and the study professionals, and wherein the Studies Module uses a blockchain process to immutably monitor, record, track and audit compliance with applicable regulations and guidelines, and wherein the network system compiles and stores an immutable studies audit trail in the system database.

16. The network system according to claim 15, wherein the Studies Module incorporates an authentication process for access to study data and study documents, based on respective permissions associated with the study participants, the study staff and the study professionals.

17. The network system according to claim 16, wherein the Studies Module incorporates a compliance process, which automatically updates relevance regulatory requirements, standards, guidelines and forms, associates requisite study documents and requisite study forms for each of multiple study categories, and automatically updates the requisite study documents and the requisite study forms to current versions.

18. The network system according to claim 17, wherein the Studies Module incorporates a live chat function, which enables communications between and among the study participants, the study staff, the study professionals, and one or more study supervisors, and which tracks activities of the study participants, the study staff and the study professionals, and which obtains required informed consent from the study participants.

19. The network system according to claim 18, wherein the Studies Module uses a blockchain process to immutably monitor, record, track and audit the authentication process, the compliance process and the live chat functions, and to provide audited risk management, and wherein the network system compiles and stores an immutable risk audit trail in the system database.

20. The network system according to claim 19, wherein the Studies Module provides instructions to the enterprise users regarding credentials-based selections of multiple studies team members comprising the one or more study supervisors, the study staff and the study professionals, and wherein profiles of the studies team members uploaded to the Web App can be viewed by authorized studies team members, and wherein the Studies Module provides specific instructions to the studies team members as to how to conduct assigned tasks in the enterprise studies.

* * * * *